(12) United States Patent
Kugler et al.

(10) Patent No.: US 9,717,889 B2
(45) Date of Patent: Aug. 1, 2017

(54) ENDOVASCULAR DEVICES AND METHODS FOR EXPLOITING INTRAMURAL SPACE

(71) Applicant: BridgePoint Medical, Inc., Plymouth, MN (US)

(72) Inventors: Chad J. Kugler, Buffalo, MN (US);
Matthew J. Olson, Crystal, MN (US);
Ross A. Olson, Anoka, MN (US);
David B. Robinson, Chanhassen, MN (US)

(73) Assignee: BridgePoint Medical, Inc., Plymouth, MN (US)

( * ) Notice: Subject to any disclaimer, the term of this patent is extended or adjusted under 35 U.S.C. 154(b) by 0 days.

(21) Appl. No.: 14/696,928

(22) Filed: Apr. 27, 2015

(65) Prior Publication Data

US 2015/0231373 A1    Aug. 20, 2015

Related U.S. Application Data

(63) Continuation of application No. 12/222,737, filed on Aug. 14, 2008, now Pat. No. 9,060,802, which is a continuation-in-part of application No. PCT/US2007/024209, filed on Nov. 20, 2007.

(60) Provisional application No. 60/964,765, filed on Aug. 14, 2007, provisional application No. 60/905,849, (Continued)

(51) Int. Cl.
*A61M 25/10* (2013.01)

(52) U.S. Cl.
CPC .................... *A61M 25/10* (2013.01)

(58) Field of Classification Search
CPC ............ A61B 17/3478; A61B 17/3207; A61B 2017/22048; A61B 2017/22054; A61B 2017/22069; A61B 2017/22094; A61B 2017/22095; A61B 2017/00252;
(Continued)

(56) References Cited

U.S. PATENT DOCUMENTS

| 4,020,829 A | 5/1977 | Willson et al. |
| 4,233,983 A | 11/1980 | Rocco |
| 4,569,347 A | 2/1986 | Frisbie |

(Continued)

FOREIGN PATENT DOCUMENTS

| WO | 0178822 A2 | 10/2001 |
| WO | 2007033052 A2 | 3/2007 |

(Continued)

OTHER PUBLICATIONS

Bolia, Amman, "Subintimal Angioplasty: Which Cases et Choose, How to Avoid Pitfalls and Technical Tips", Combined Session: Vascular Surgery and Interventional Radiology, pp. III 8.1-III 8.3.
(Continued)

*Primary Examiner* — Katrina Stransky
(74) *Attorney, Agent, or Firm* — Seager, Tufte & Wickhem LLP

(57) ABSTRACT

The present disclosure is directed to a device. The device may include a distal shaft defining a central lumen and an orienting element comprising at least one inflatable member. Wherein a first portion of the orienting element extending from the shaft in a first direction and a second portion of the orienting element extending from the shaft in a second direction. Further, wherein the second direction is substantially opposite the first direction.

19 Claims, 21 Drawing Sheets

Related U.S. Application Data filed on Mar. 9, 2007, provisional application No. 60/860,416, filed on Nov. 21, 2006.

(58) Field of Classification Search
CPC ...... A61M 25/1002; A61M 2025/1059; A61M 25/0125; A61M 25/10
USPC ..... 606/191, 192, 194, 198, 190; 604/96.01, 604/101.01–101.05, 103.07
See application file for complete search history.

(56) References Cited

U.S. PATENT DOCUMENTS

| | | |
|---|---|---|
| 4,581,017 A | 4/1986 | Sahota |
| 4,621,636 A | 11/1986 | Fogarty |
| 4,747,821 A | 5/1988 | Kensey et al. |
| 4,762,130 A | 8/1988 | Fogarty et al. |
| 4,774,949 A | 10/1988 | Fogarty |
| 4,819,634 A | 4/1989 | Shiber |
| 4,878,495 A | 11/1989 | Grayzel |
| 4,976,689 A | 12/1990 | Buchbinder et al. |
| 4,979,939 A | 12/1990 | Shiber |
| 4,990,134 A | 2/1991 | Auth |
| 5,071,406 A | 12/1991 | Jang |
| 5,127,917 A | 7/1992 | Niederhauser et al. |
| 5,193,546 A | 3/1993 | Shaknovich |
| 5,201,753 A | 4/1993 | Lampropoulos et al. |
| 5,263,493 A | 11/1993 | Avitall |
| 5,275,610 A | 1/1994 | Eberbach |
| 5,324,263 A | 6/1994 | Kraus et al. |
| 5,356,418 A | 10/1994 | Shturman |
| 5,372,587 A | 12/1994 | Hammerslag et al. |
| 5,383,856 A | 1/1995 | Bersin |
| 5,385,152 A | 1/1995 | Abele et al. |
| 5,409,453 A | 4/1995 | Lundquist et al. |
| 5,415,637 A | 5/1995 | Khosravi |
| 5,464,395 A * | 11/1995 | Faxon ............... A61M 25/0084 604/103.02 |
| 5,501,667 A | 3/1996 | Verduin, Jr. |
| 5,505,702 A | 4/1996 | Arney |
| 5,534,007 A | 7/1996 | St. Germain et al. |
| 5,555,883 A | 9/1996 | Avitall |
| 5,571,122 A | 11/1996 | Kelly et al. |
| 5,571,169 A | 11/1996 | Plaia et al. |
| 5,603,720 A | 2/1997 | Kieturakis et al. |
| 5,643,298 A | 7/1997 | Nordgren et al. |
| 5,645,529 A | 7/1997 | Fagan et al. |
| 5,655,548 A | 8/1997 | Nelson et al. |
| 5,695,506 A | 12/1997 | Pike et al. |
| 5,728,133 A | 3/1998 | Kontos |
| 5,741,270 A | 4/1998 | Hansen et al. |
| 5,741,429 A | 4/1998 | Donadio, III et al. |
| 5,779,721 A | 7/1998 | Nash |
| 5,807,241 A | 9/1998 | Heimberger |
| 5,824,071 A | 10/1998 | Nelson et al. |
| 5,830,222 A | 11/1998 | Makower |
| 5,830,224 A | 11/1998 | Cohn et al. |
| 5,843,050 A | 12/1998 | Jones et al. |
| 5,910,133 A | 6/1999 | Gould |
| 5,916,194 A | 6/1999 | Jacobsen et al. |
| 5,935,108 A | 8/1999 | Katoh et al. |
| 5,944,686 A | 8/1999 | Patterson et al. |
| 5,954,713 A | 9/1999 | Newman et al. |
| 5,957,900 A | 9/1999 | Ouchi |
| 5,968,064 A | 10/1999 | Selmon et al. |
| 5,989,276 A | 11/1999 | Houser et al. |
| 6,010,449 A | 1/2000 | Selmon et al. |
| 6,013,055 A | 1/2000 | Bampos et al. |
| 6,015,405 A | 1/2000 | Schwartz et al. |
| 6,022,343 A | 2/2000 | Johnson et al. |
| 6,036,707 A | 3/2000 | Spaulding |
| 6,036,717 A | 3/2000 | Mers Kelly et al. |
| 6,059,750 A | 5/2000 | Fogarty et al. |
| 6,068,638 A | 5/2000 | Makower |
| 6,071,281 A | 6/2000 | Burnside et al. |
| 6,071,292 A | 6/2000 | Makower et al. |
| 6,081,738 A | 6/2000 | Hinohara et al. |
| 6,099,542 A | 8/2000 | Cohn et al. |
| 6,117,064 A | 9/2000 | Apple et al. |
| 6,120,516 A | 9/2000 | Selmon et al. |
| 6,126,649 A | 10/2000 | VanTassel et al. |
| 6,155,264 A | 12/2000 | Ressemann et al. |
| 6,157,852 A | 12/2000 | Selmon et al. |
| 6,159,225 A | 12/2000 | Makower |
| 6,183,432 B1 | 2/2001 | Milo |
| 6,186,972 B1 | 2/2001 | Nelson et al. |
| 6,190,353 B1 | 2/2001 | Makower et al. |
| 6,203,559 B1 | 3/2001 | Davis et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,246,914 B1 | 6/2001 | de la Rama et al. |
| 6,248,121 B1 | 6/2001 | Nobles |
| 6,254,588 B1 | 7/2001 | Jones et al. |
| 6,258,052 B1 | 7/2001 | Milo |
| 6,266,550 B1 | 7/2001 | Selmon et al. |
| 6,277,133 B1 | 8/2001 | Kanesaka |
| 6,283,940 B1 | 9/2001 | Mulholland |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,337,142 B2 | 1/2002 | Harder et al. |
| 6,358,244 B1 | 3/2002 | Newman et al. |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,398,798 B2 | 6/2002 | Selmon et al. |
| 6,416,523 B1 | 7/2002 | Lafontaine |
| 6,428,552 B1 | 8/2002 | Sparks |
| 6,432,127 B1 | 8/2002 | Kim et al. |
| 6,447,539 B1 | 9/2002 | Nelson et al. |
| 6,475,226 B1 | 11/2002 | Belef et al. |
| 6,485,458 B1 | 11/2002 | Takahashi |
| 6,491,660 B2 | 12/2002 | Guo et al. |
| 6,491,707 B2 | 12/2002 | Makower et al. |
| 6,506,178 B1 | 1/2003 | Schubart et al. |
| 6,508,824 B1 | 1/2003 | Flaherty et al. |
| 6,508,825 B1 | 1/2003 | Selmon et al. |
| 6,511,458 B2 * | 1/2003 | Milo .................. A61B 17/3207 600/585 |
| 6,514,217 B1 | 2/2003 | Selmon et al. |
| 6,544,230 B1 | 4/2003 | Flaherty et al. |
| 6,561,998 B1 | 5/2003 | Roth et al. |
| 6,565,583 B1 | 5/2003 | Deaton et al. |
| 6,569,143 B2 | 5/2003 | Alchas et al. |
| 6,569,145 B1 | 5/2003 | Shmulewitz et al. |
| 6,569,150 B2 | 5/2003 | Teague et al. |
| 6,579,311 B1 | 6/2003 | Makower |
| 6,589,164 B1 | 7/2003 | Flaherty |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |
| 6,623,448 B2 | 9/2003 | Slater |
| 6,638,247 B1 | 10/2003 | Selmon et al. |
| 6,638,293 B1 | 10/2003 | Makower et al. |
| 6,655,386 B1 | 12/2003 | Makower et al. |
| 6,656,195 B2 | 12/2003 | Peters et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,444 B1 | 3/2004 | Makower |
| 6,719,725 B2 | 4/2004 | Milo et al. |
| 6,726,677 B1 | 4/2004 | Flaherty et al. |
| 6,746,426 B1 | 6/2004 | Flaherty et al. |
| 6,746,462 B1 | 6/2004 | Selmon et al. |

(56) References Cited

U.S. PATENT DOCUMENTS

| | | |
|---|---|---|
| 6,746,464 B1 | 6/2004 | Makower |
| 6,786,884 B1 | 9/2004 | DeCant, Jr. et al. |
| 6,800,085 B2 | 10/2004 | Selmon et al. |
| 6,824,550 B1 | 11/2004 | Noriega et al. |
| 6,830,577 B2 | 12/2004 | Nash et al. |
| 6,837,868 B1 | 1/2005 | Fajnsztajn |
| 6,860,892 B1 | 3/2005 | Tanaka et al. |
| 6,863,684 B2 | 3/2005 | Kim et al. |
| 6,866,676 B2 | 3/2005 | Kieturakis et al. |
| 6,884,225 B2 | 4/2005 | Kato et al. |
| 6,905,505 B2 | 6/2005 | Nash et al. |
| 6,929,009 B2 | 8/2005 | Makower et al. |
| 6,936,056 B2 | 8/2005 | Nash et al. |
| 6,942,641 B2 | 9/2005 | Seddon |
| 6,949,125 B2 | 9/2005 | Robertson |
| 6,991,617 B2 | 1/2006 | Hektner et al. |
| 7,004,173 B2 | 2/2006 | Sparks et al. |
| 7,056,325 B1 | 6/2006 | Makower et al. |
| 7,059,330 B1 | 6/2006 | Makower et al. |
| 7,083,588 B1 | 8/2006 | Shmulewitz et al. |
| 7,094,230 B2 | 8/2006 | Flaherty et al. |
| 7,105,031 B2 | 9/2006 | Letort |
| 7,134,438 B2 | 11/2006 | Makower et al. |
| 7,137,990 B2 | 11/2006 | Hebert et al. |
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Garibotto et al. |
| 7,377,910 B2 | 5/2008 | Katoh et al. |
| 7,465,286 B2 | 12/2008 | Patterson et al. |
| 2001/0000041 A1 | 3/2001 | Selmon et al. |
| 2001/0056273 A1 | 12/2001 | C |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1* | 6/2003 | Jen ............... A61B 17/3207 600/585 |
| 2003/0120195 A1 | 6/2003 | Milo et al. |
| 2003/0167038 A1 | 9/2003 | Yozu et al. |
| 2003/0236542 A1 | 12/2003 | Makower |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1 | 8/2004 | Simpson et al. |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |
| 2005/0075662 A1 | 4/2005 | Pedersen et al. |
| 2005/0171478 A1 | 8/2005 | Selmon et al. |
| 2005/0177105 A1 | 8/2005 | Shalev |
| 2005/0216044 A1 | 9/2005 | Hong |
| 2005/0261663 A1 | 11/2005 | Patterson et al. |
| 2006/0094930 A1 | 5/2006 | Sparks et al. |
| 2006/0135984 A1 | 6/2006 | Kramer et al. |
| 2006/0229646 A1 | 10/2006 | Sparks |
| 2006/0271078 A1 | 11/2006 | Modesitt |
| 2007/0083220 A1 | 4/2007 | Shamay |
| 2007/0088230 A1 | 4/2007 | Terashi et al. |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0093783 A1 | 4/2007 | Kugler et al. |
| 2007/0265596 A1 | 11/2007 | Jen et al. |
| 2008/0103443 A1 | 5/2008 | Kabrick et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2009/0088685 A1 | 4/2009 | Kugler et al. |
| 2009/0124899 A1 | 5/2009 | Jacobs et al. |
| 2009/0209910 A1 | 8/2009 | Kugler et al. |
| 2009/0270890 A1 | 10/2009 | Robinson et al. |
| 2010/0063534 A1 | 3/2010 | Kugler et al. |
| 2010/0069945 A1 | 3/2010 | Olson et al. |

FOREIGN PATENT DOCUMENTS

| | | |
|---|---|---|
| WO | 2008063621 A2 | 5/2008 |
| WO | 2009054943 A1 | 4/2009 |
| WO | 2009100129 A2 | 8/2009 |
| WO | 2009134346 A2 | 11/2009 |
| WO | 2010019241 A1 | 2/2010 |
| WO | 2010044816 A1 | 4/2010 |

OTHER PUBLICATIONS

Colombo, Antonio et al., "Treating Chronic Total Occlusions Using Subintimal Tracking and Reentry: the STAR Technique," Catheterization and Cardiovascular Interventions, vol. 64: 407-411, 2005.

International Report on Patentability for PCT/US07/24209, 9 pages, issued on May 26, 2009.

International Search Report for PCT/US07/24209, 8 pages, issued on Jul. 9, 2008.

* cited by examiner

ENDOVASCULAR DEVICES AND METHODS FOR EXPLOITING INTRAMURAL SPACE

CROSS-REFERENCE TO RELATED APPLICATION

This application is a continuation of U.S. patent application Ser. No. 12/222,737, filed Aug. 14, 2008, which is a continuation-in-part of PCT International Application No. PCT/US2007/024209, filed Nov. 20, 2007, which claims the benefit of U.S. Provisional Application No. 60/964,765, filed Aug. 14, 2007, U.S. Provisional Application No. 60/905,849, filed Mar. 9, 2007, and U.S. Provisional Application No. 60/860,416, filed Nov. 21, 2006, each of which are herein incorporated by reference in their entirety.

FIELD OF THE INVENTION

The inventions described herein relate to devices and associated methods for the treatment of chronic total occlusions. More particularly, the inventions described herein relate to devices and methods for crossing chronic total occlusions and establishing a pathway blood flow past the chronic total occlusions.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, cannot accurately direct endovascular devices toward the visualized lumen, or fail to advance devices through the lesion. Bypass surgery is often the preferred treatment for patients with chronic total occlusions, but less invasive techniques would be preferred.

BRIEF DESCRIPTION OF THE FIGURES

In FIG. 2, a total occlusion is shown within a coronary artery.

In FIG. 3, the wall of the blood vessel is shown having three layers (the intima, the media, and the adventitia).

In FIG. 4, an orienting device is shown disposed between the adventitia and the intima of the artery.

BRIEF SUMMARY

Described herein are devices and methods employed to exploit the vascular wall of a vascular lumen for the purpose of bypassing a total occlusion of an artery. Exploitation of a vascular wall may involve the passage of an endovascular device into and out of said wall which is commonly and interchangeably described as false lumen access, intramural access, submedial access or in the case of this disclosure, subintimal access.

In one aspect, the present disclosure is directed to a device. The device may include a distal shaft defining a central lumen and an orienting element comprising at least one inflatable member. Wherein a first portion of the orienting element extending from the shaft in a first direction and a second portion of the orienting element extending from the shaft in a second direction. Further, wherein the second direction is substantially opposite the first direction.

In another aspect, the present disclosure is directed to a device. The device may include a distal shaft defining a central lumen and an orienting element comprising a first inflatable member and a second inflatable member. Wherein the first inflatable member extending from the shaft in a first direction and the second inflatable member extending from the shaft in a second direction. Further, wherein the second direction is substantially opposite the first direction.

In yet another aspect, the present disclosure is directed to a method. The method may include providing a device comprising a distal shaft and an orienting element, and positioning the orienting element of the device between an occlusion and an adventitia of a blood vessel. The method may further include inflating an inflatable member of the orienting element to orient the device relative to a true lumen of the blood vessel, and advancing a re-entry device through a lumen defined by the device. The method may still further include advancing a distal end of a re-entry device through an aperture of the device, and wherein the aperture is substantially orthogonal to a plane defined by the orienting element.

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1:
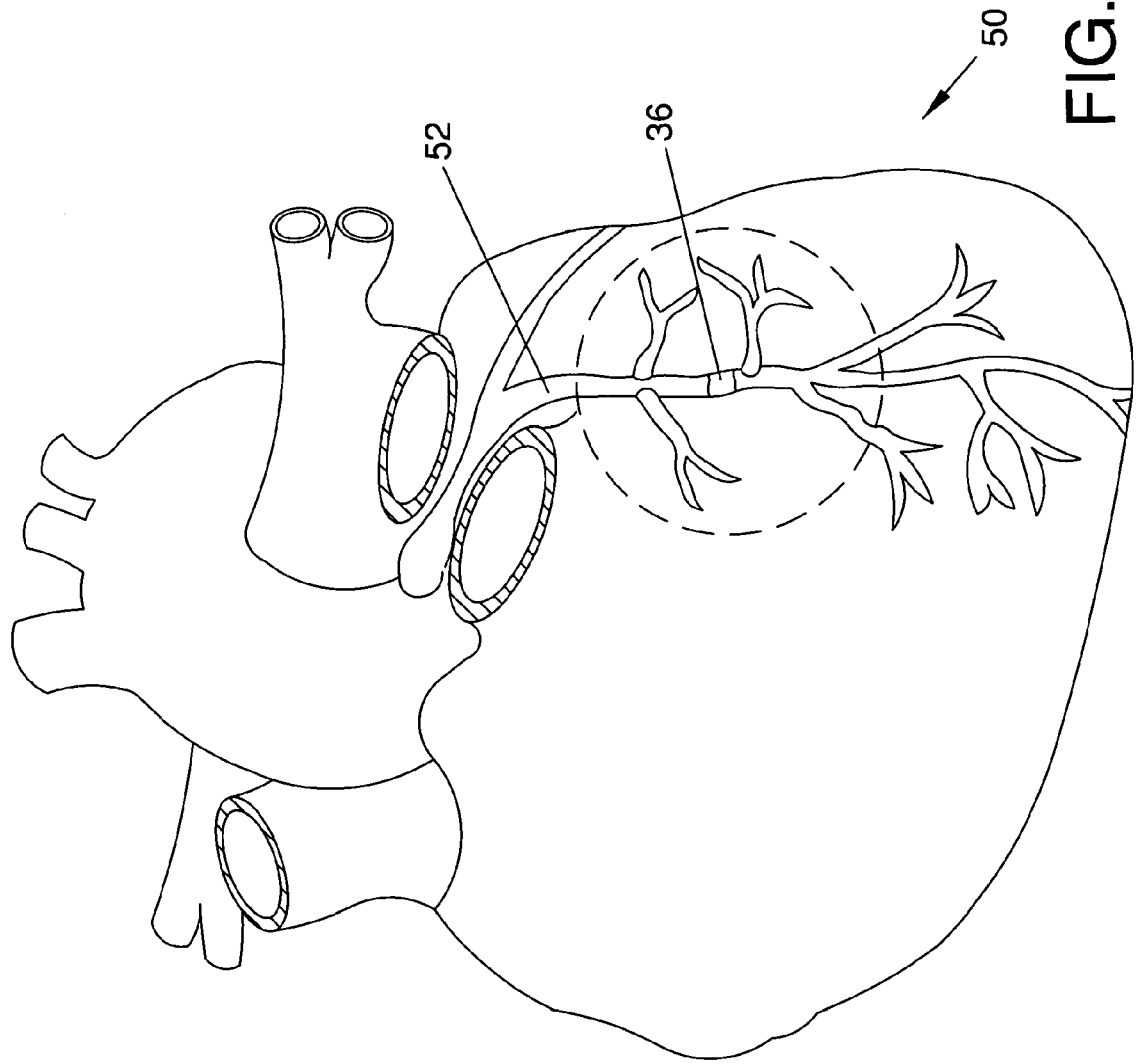
FIG. 1 is a somewhat stylized representation of a human heart. The heart includes a plurality of coronary arteries, all of which are susceptible to occlusion.

FIG. 1 is a somewhat stylized representation of a human heart 50. Heart 50 includes a plurality of coronary arteries 52, all of which are susceptible to occlusion. Under certain physiological circumstances and given sufficient time, some occlusions may become total or complete, such as total occlusion 36. As used herein, the terms total occlusion and complete occlusion are intended to refer to the same or similar degree of occlusion with some possible variation in the age of the occlusion. Generally, a total occlusion refers to a vascular lumen that is ninety percent or more functionally occluded in cross-sectional area, rendering it with little to no blood flow therethrough and making it difficult or impossible to pass a conventional guide wire therethrough. Also generally, the older the total occlusion the more organized the occlusive material will be and the more fibrous and calcified it will become. According to one accepted clinical definition, a total occlusion is considered chronic if it is greater than two weeks old from symptom onset.

Figure 2:
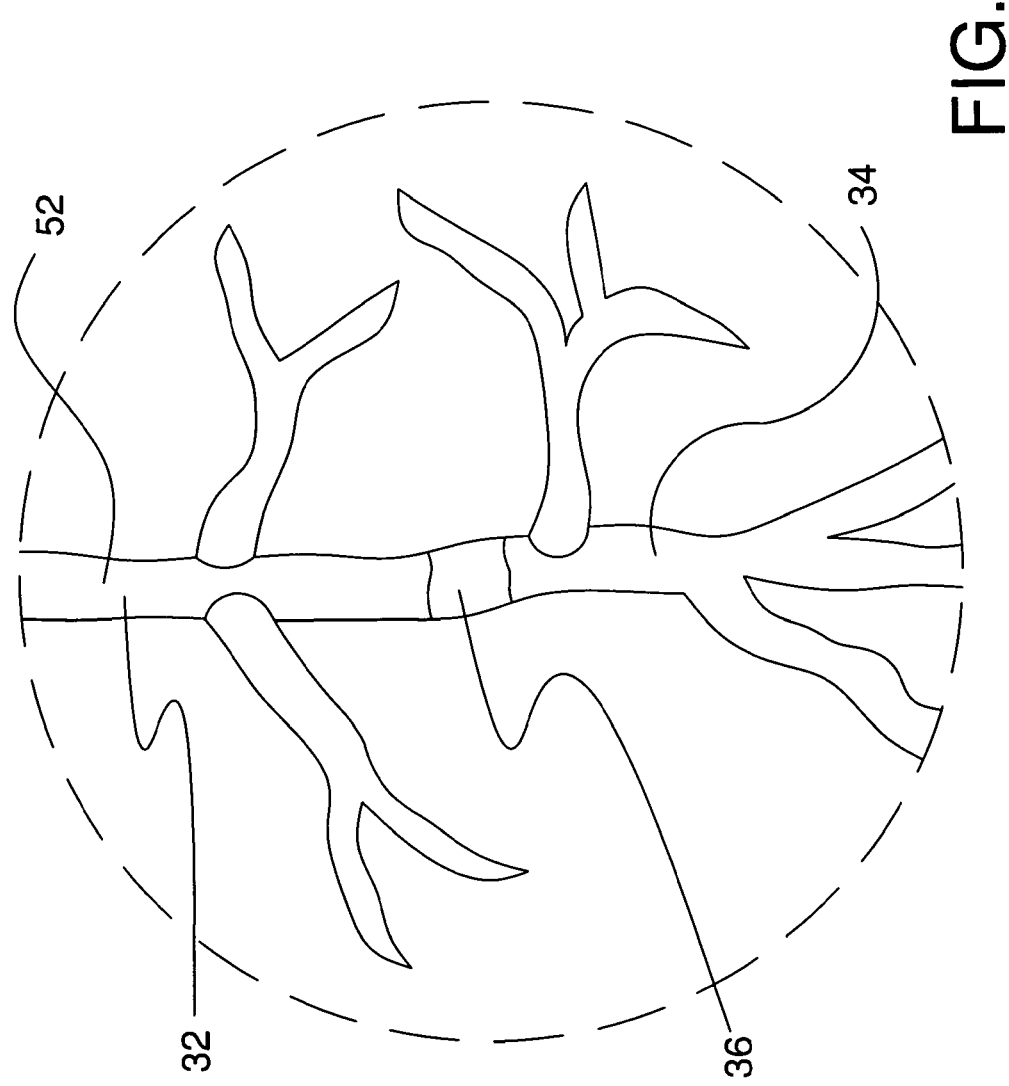
FIG. 2 is an enlarged view further illustrating a portion of the heart shown in the previous figure.

FIG. 2 is an enlarged view further illustrating a portion of heart 50 shown in the previous figure. In FIG. 2, a total occlusion 36 is shown within a coronary artery 52. Generally, the proximal segment 32 of artery 52 (i.e., the portion of artery 52 proximal of total occlusion 36) may be easily accessed using endovascular devices and has adequate blood flow to supply the surrounding cardiac muscle. The distal segment 34 of artery 52 (i.e., the portion of artery 52 distal of total occlusion 36) is not easily accessed with interventional devices and has significantly reduced blood flow as compared to proximal segment 32.

Figure 3:
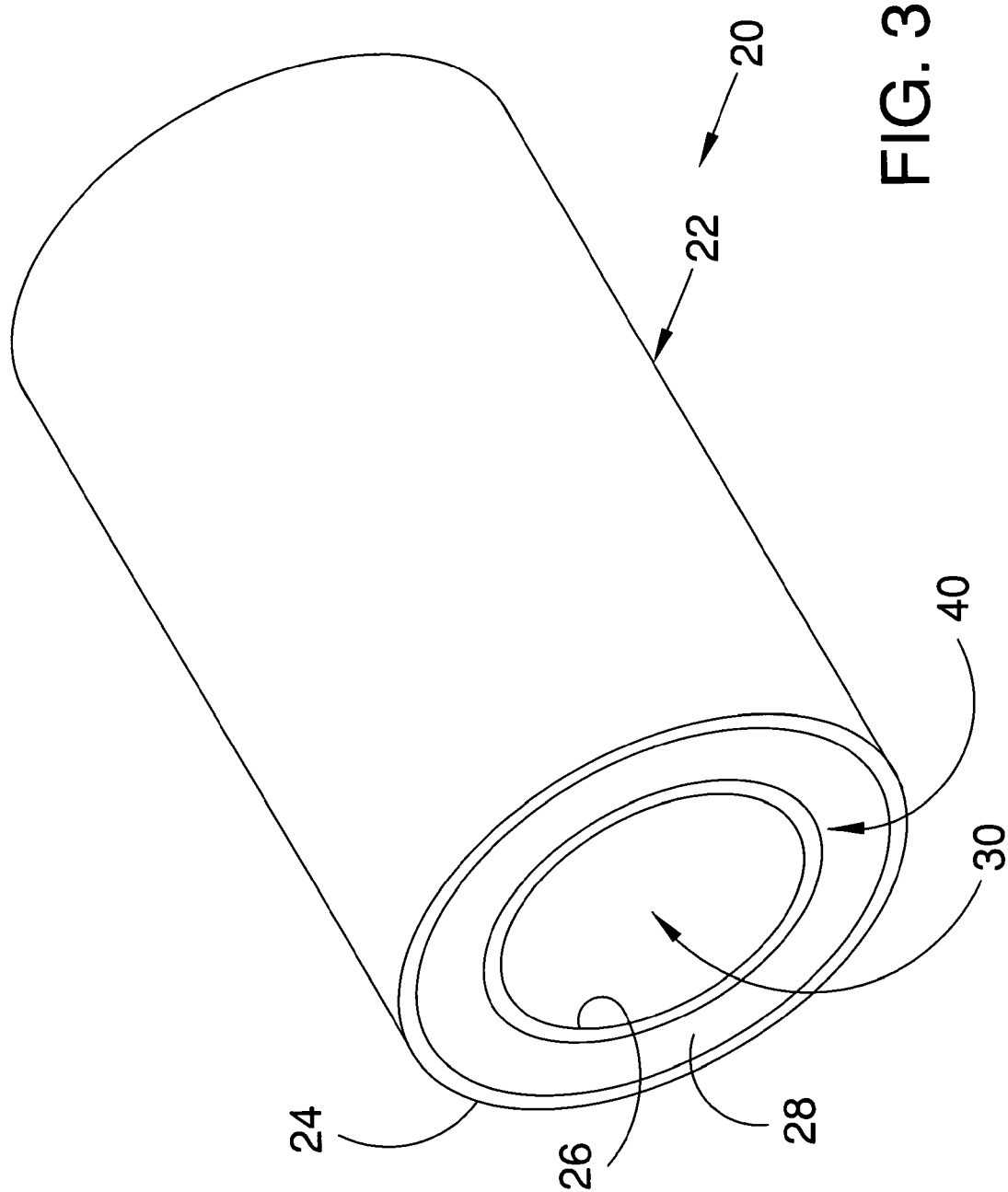
FIG. 3 is a perspective view of a blood vessel (e.g., a coronary artery).

FIG. 3 is a perspective view of an artery 20 having a wall 22. In FIG. 3, wall 22 of artery 20 is shown having three layers. The outermost layer of wall 22 is the adventitia 24 and the innermost layer of wall 22 is the intima 26. Intima 26 defines a true lumen 30 of artery 20. The tissues extending between intima 26 and adventitia 24 may be collectively referred to as the media 28. For purposes of illustration, intima 26, media 28 and adventitia 24 are each shown as a single homogenous layer in FIG. 3. In the human body, however, the intima and the media each comprise a number of sub-layers. The transition between the external most portion of the intima and the internal most portion of the media is sometimes referred to as the subintimal space 40.

With reference to FIG. 3, it will be appreciated that the subintimal space 40 has a generally annular shape with its radial center at the center of the true lumen. Some of the devices and methods discussed in this detailed description may take advantage of the position and geometry of the subintimal space 40 relative to the true lumen of the blood vessel. For example, some orienting devices described herein may be adapted to orient themselves within that space. Once the orientation of the orienting device is established, the orienting device may be used to direct a re-entry device toward the true lumen.

Figure 4:
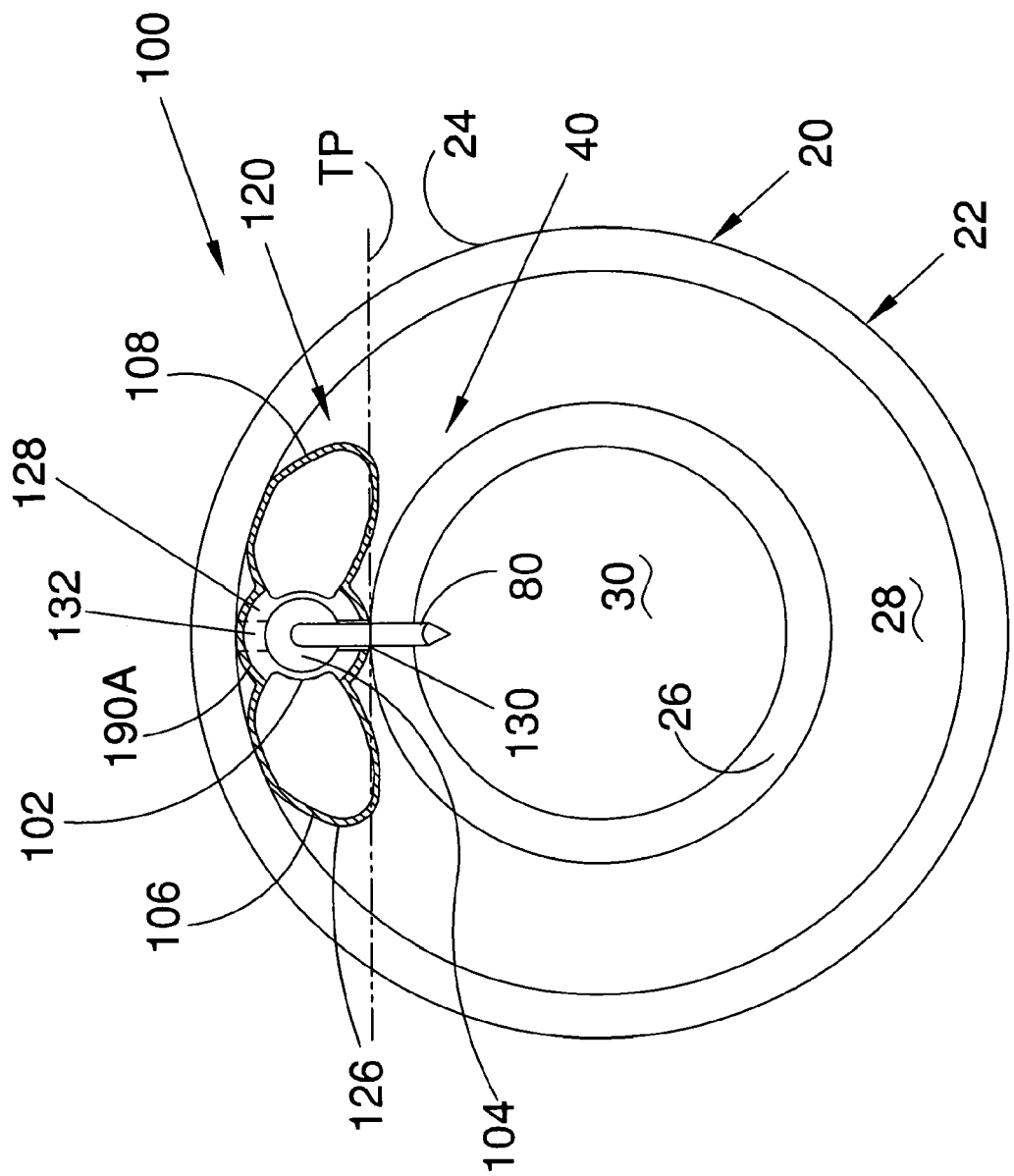
FIG. 4 is a lateral cross-sectional view of the artery shown in the previous figure.

FIG. 4 is a lateral cross-sectional view of artery 20 shown in the previous figure. In FIG. 4, an orienting device 100 is shown disposed between adventitia 24 and intima 26 of artery 20. Orienting device 100 comprises a distal shaft 102 having an outer wall 128 defining a central lumen 104. Orienting device 100 comprises an orienting element 120 that is coupled to distal shaft 102.

In the embodiment of FIG. 4, orienting element 120 comprises an inflatable member 126. The top of inflatable member 126 may be fixed to distal shaft 102, for example, at a first interface 190A. The bottom of inflatable member 126 may be fixed to distal shaft 102, for example, at a second interface 190B.

Orienting element 120 comprises a first portion 106 and a second portion 108. First portion 106 of orienting element 120 extends in a first direction away from distal shaft 102. Second portion 108 of orienting element 120 extends away from distal shaft 102 in a second direction that is generally opposite the first direction.

Distal shaft 102 defines a first aperture 130 and a second aperture 132. First aperture 130 extends in a third direction through distal shaft 102. A second aperture 132 extends through distal shaft 102 in a forth direction that is generally opposite the third direction. The first aperture 130 and second aperture 132 are generally oriented at a right angle to a tangent plane TP. In FIG. 4, tangent plane TP is tangent to subintimal space 40.

When inflatable member 126 of orienting element 120 is inflated between adventitia 24 and intima 26 of artery 20 orienting device 100 will orient itself within artery 20 so that either first aperture 130 or second aperture 132 opens toward a true lumen of the artery. In the embodiment of FIG. 4, orienting device 100 has been positioned so that first aperture 130 opens toward intima 26 of artery 20 and second aperture 132 opens toward adventitia 24. In FIG. 4, a re-entry device 80 is shown extending through first aperture 130 and intima 26. A distal end of re-entry device 80 is disposed in true lumen 30 of blood vessel 20.

When inflatable member 126 is inflated, the number of directions that first aperture 130 and second aperture 132 may be facing is reduced. This may be conceptualized in terms of degrees of freedom. When inflatable member 126 of orienting element 120 is inflated, the number of directions that an aperture may be facing is reduced from 360 degrees of freedom to two degrees of freedom, 180 degrees apart. Orienting device 100 and re-entry device 80 may be used to establish fluid communication between the proximal segment and the distal segment that are separated by an occlusion. Exemplary methods may be described with reference to FIGS. 5 through 13.

Figure 5:
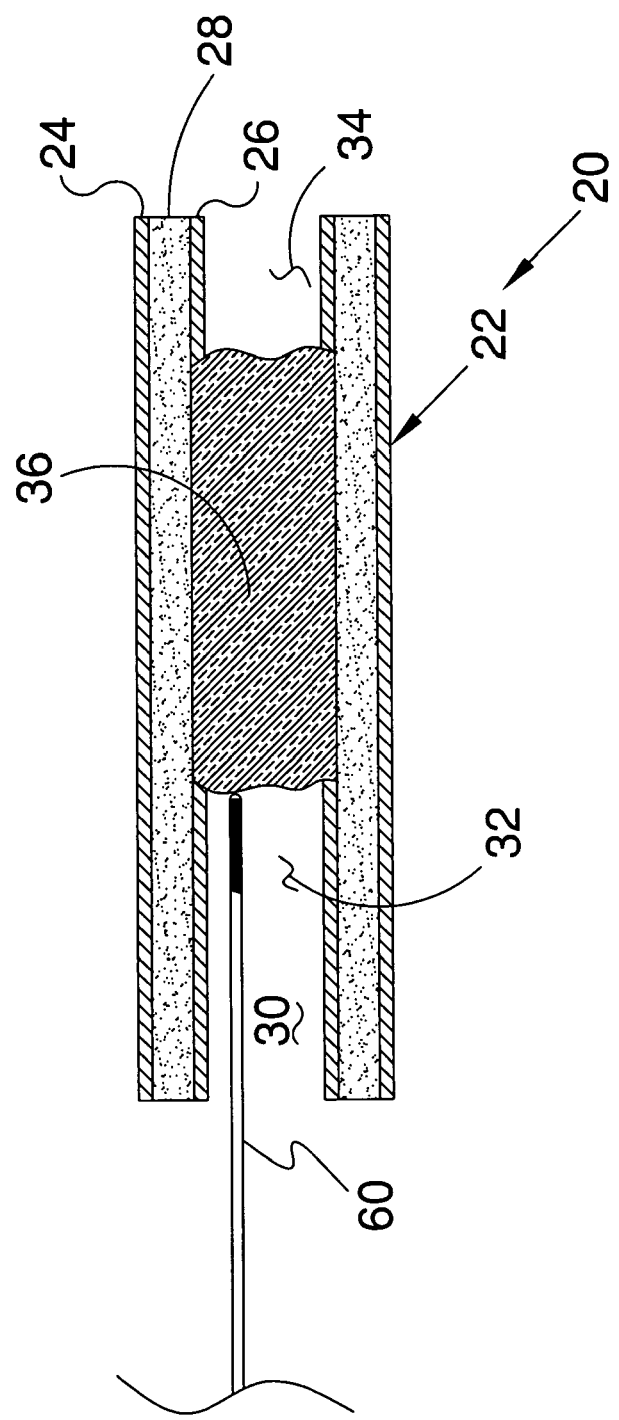
FIG. 5 is a longitudinal cross-sectional view of an artery having an occlusion blocking the true lumen.

FIG. 5 is a longitudinal cross-sectional view of an artery 20 having an occlusion 36 blocking true lumen 30 thereof. Occlusion 36 divides true lumen 30 into a proximal segment 32 and a distal segment 34. In FIG. 5, a distal portion of a guidewire 60 is shown extending into proximal segment 32 of true lumen 30. The methods described in this document may include the step of advancing a guidewire to a location proximate an occlusion in a blood vessel. The exemplary methods described in this document may also include the step of advancing guidewire 60 between occlusion 36 and adventitia 24 of wall 22. In some cases, however, the nature of the occlusion and the blood vessel will be such that the guidewire is unlikely to advance beyond the occlusion. When this is the case, the guidewire may be used to guide additional endovascular devices to a location proximate occlusion 36.

Figure 6:
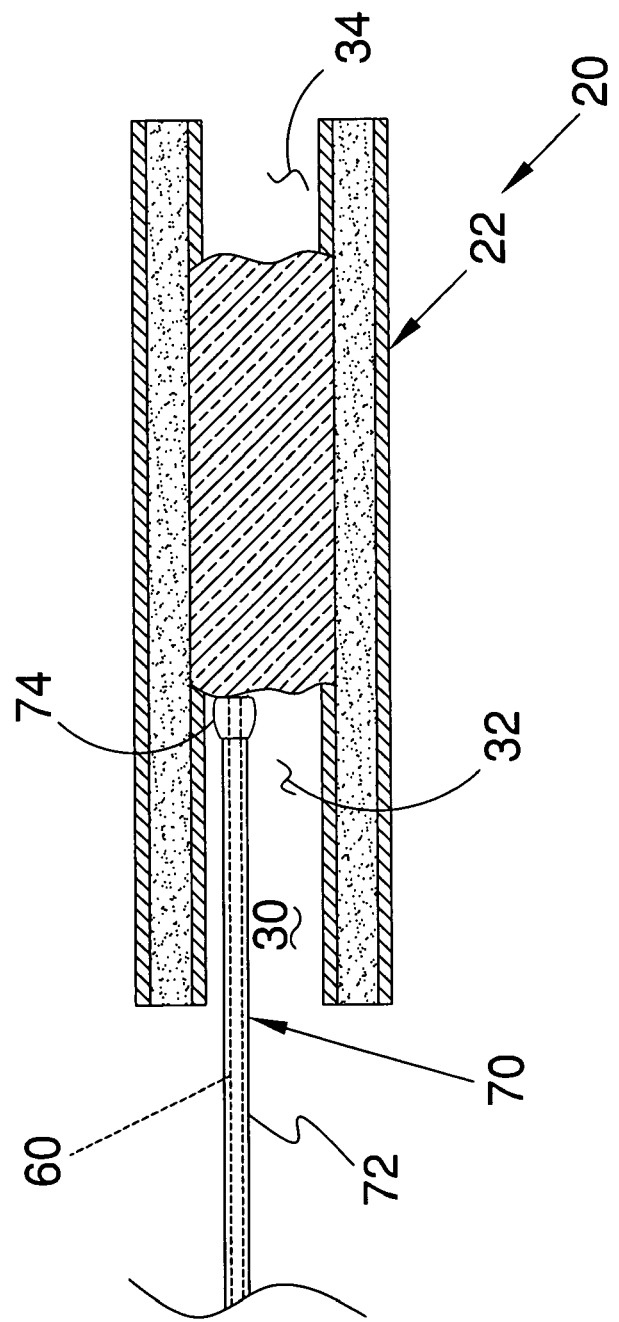
FIG. 6 is an additional cross-sectional view of the artery shown in the previous figure. In the embodiment of FIG. 6, a crossing device has been advanced over a guidewire so that a distal portion of crossing device is disposed in proximal segment of the true lumen.

FIG. 6 is an additional cross-sectional view of artery 20 shown in the previous figure. In the embodiment of FIG. 6, a crossing device 70 has been advanced over guidewire 60 so that a distal portion of crossing device 70 is disposed in proximal segment 32 of true lumen 30. Crossing device 70 of FIG. 6 comprises a tip 74 that is fixed to a distal end of a shaft 72. Crossing device 70 may be used in conjunction with a method for establishing a channel between proximal segment 32 and distal segment 34. The methods described in this document may include the step of advancing a crossing device over a guidewire.

In some useful methods in accordance with the present disclosure, crossing device 70 may be rotated about its longitudinal axis and moved in a direction parallel to its longitudinal axis simultaneously. When this is the case, rotation of crossing device 70 may reduce resistance to the axial advancement of crossing device 70. These methods take advantage of the fact that the kinetic coefficient of friction is usually less than the static coefficient of friction for a given frictional interface. Rotating crossing device 70 assures that the coefficient of friction at the interface between the crossing device and the surround tissue will be a kinetic coefficient of friction and not a static coefficient of friction.

Figure 7:
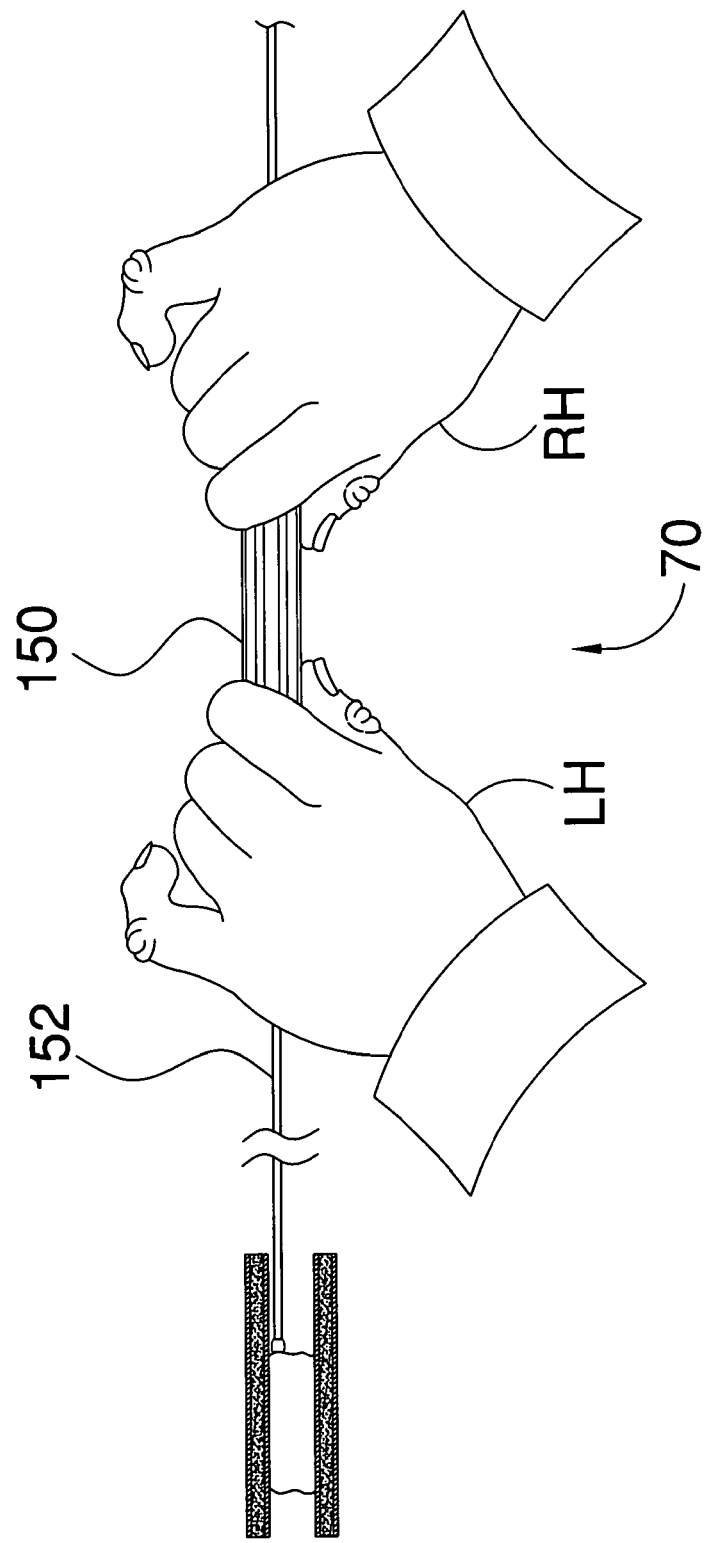
FIG. 7 is a plan view showing an assembly including crossing device shown in the previous figure.

FIG. 7 is a plan view showing an assembly including crossing device 70 shown in the previous figure. In the embodiment of FIG. 7, a handle assembly 150 is coupled to crossing device 70. In FIG. 7, handle assembly 150 is shown disposed about a proximal portion of a shaft 152 of crossing device 70. In FIG. 7, a portion of handle assembly 150 is positioned between the thumb and forefinger of a left hand LH. A second portion of handle assembly 150 is disposed between the thumb and forefinger of a right hand RH. With reference to FIG. 7, it will be appreciated that handle assembly 150 is long enough to receive the thumb and forefingers of a physician's right and left hands. When this is the case, a physician can use two hands to rotate handle assembly 150.

Rotation of crossing device 70 can be achieved by rolling handle assembly 150 between the thumb and forefinger of one hand. Two hands may also be used to rotate handle assembly 150 as shown in FIG. 7. In some useful methods, crossing device 70 can be rotated and axially advanced simultaneously.

In some useful methods in accordance with the present disclosure, crossing device 70 is rotated at a rotational speed of between about 2 revolutions per minute and about 200 revolutions per minute. In some particularly useful methods in accordance with the present disclosure, crossing device 70 is rotated at a rotational speed of between about 50 revolutions per minute and about 150 revolutions per minute.

Crossing device 70 may be rotated by hand as depicted in FIG. 7. It is also contemplated that a mechanical device (e.g., an electric motor) may be used to rotate crossing device 70. Rotating crossing device 70 assures that the coefficient of friction at the interface between the crossing device and the surround tissue will be a kinetic coefficient of friction and not a static coefficient of friction.

Figure 8:
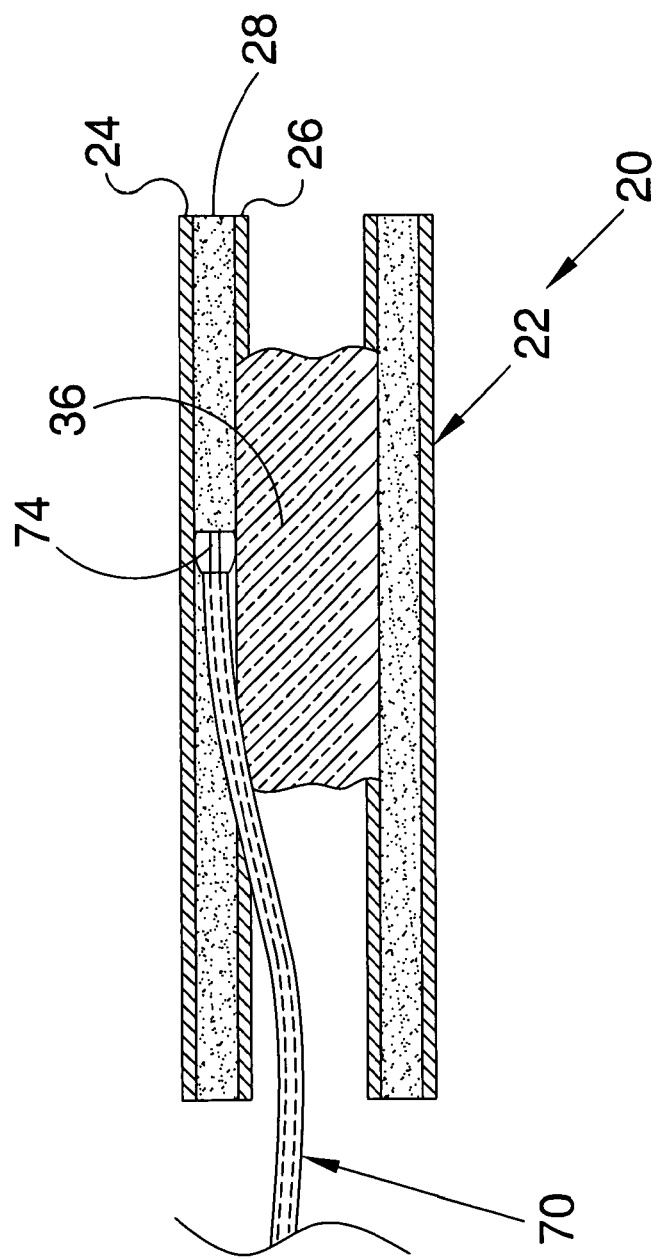
FIG. 8 is an additional view of an artery. In the embodiment of FIG. 8, the distal end of the crossing device has been advanced in a distal direction so that the tip of the crossing device is adjacent an occlusion that is blocking the true lumen of the artery.

FIG. 8 is an additional longitudinal cross-sectional view of an artery 20. In the embodiment of FIG. 8, the distal end of crossing device 70 has been advanced in a distal direction so that tip 74 is adjacent occlusion 36. With reference to FIG. 8, it will be appreciated that tip 74 has passed beyond intima 26 and is disposed between occlusion 36 and adventitia 24 of artery 20. Some methods described in this document may include the step of advancing a crossing device between an occlusion and the adventitia of an artery.

Figure 9:
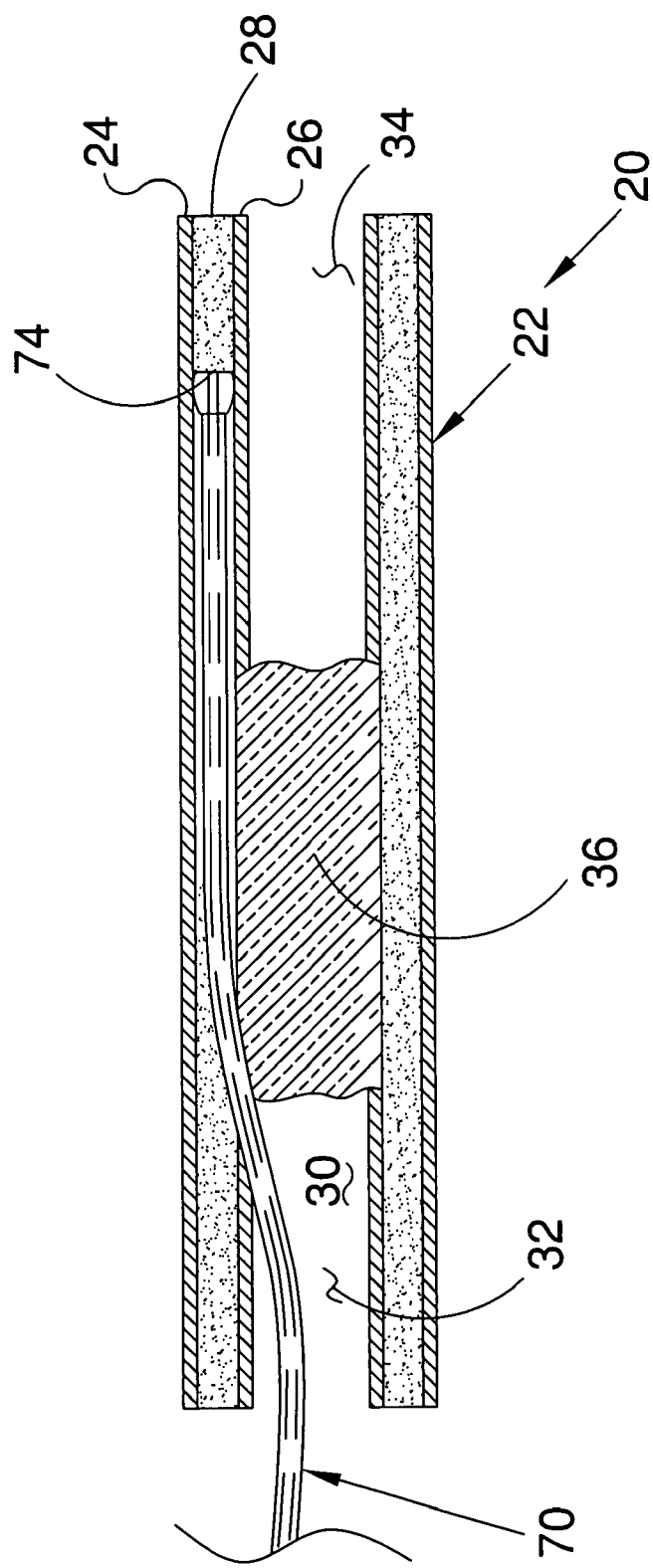
FIG. 9 is an additional view of the artery and the crossing device shown in the previous figure. In the embodiment of FIG. 9, the distal end of the crossing device has been advanced between the intima and the adventitia of the wall of the artery.

FIG. 9 is an additional view of artery 20 and crossing device 70 shown in the previous figure. In the embodiment of FIG. 9, the distal end of crossing device 70 has been advanced in an axial direction past occlusion 36. Methods described herein may include the step of advancing a crossing device beyond an occlusion. In the embodiment of FIG. 9, crossing device has crossed occlusion 36 by advancing between occlusion 36 and adventitia 24 of wall 22.

It is to be appreciated that other methods of crossing an occlusion are within the spirit and scope of this disclosure. For example, the crossing device 70 may pass through occlusion 36 while remaining disposed inside true lumen 30. In FIG. 9, tip 74 of crossing device 70 is shown residing between intima 26 and adventitia 24 of artery 20. As tip 74 moves in an axial direction between intima 26 and adventitia 24, tip 74 may cause blunt dissection of the layers forming wall 22 of artery 20. Alternatively, tip 74 may cause blunt dissection of the materials comprising the occlusion 36.

In the embodiment of FIG. 9, tip 74 of crossing device 70 is disposed between intima 26 and adventitia 24. When this is the case, fluid communication between proximal segment 32 and distal segment 34 may be achieved by creating an opening through intima 26. Such an opening may be created, for example, using a re-entry device and an orienting device that directs the advancement of the re-entry device toward intima 26.

Figure 10:
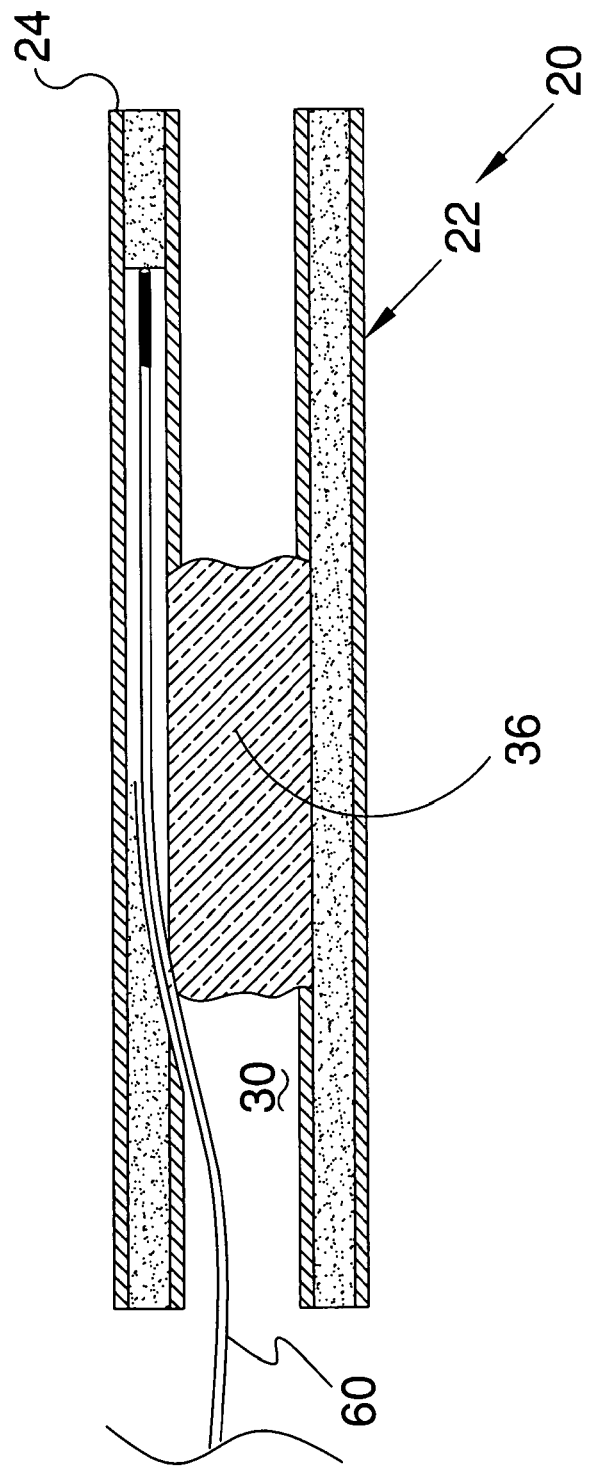
FIG. 10 is an additional view of the artery shown in the previous figure. In the embodiment of FIG. 10, the crossing device has been withdrawn and a guidewire remains in the position formerly occupied by the crossing device.

FIG. 10 is an additional view of artery 20 shown in the previous figure. In the embodiment of FIG. 10, crossing device 70 has been withdrawn from true lumen 30 of artery 20. With reference to FIG. 10, it will be appreciated that guidewire 60 remains in the position formerly occupied by crossing device 70.

The position of guidewire 60 shown in FIG. 10 may be achieved using crossing device 70. Guidewire 60 may be positioned, for example, by first placing crossing device 70 in the position shown in the previous figure, then advancing guidewire 60 through lumen 122 defined by shaft 72 of crossing device 70. Alternately, guidewire 60 may be disposed within lumen 122 while crossing device 70 is advanced beyond occlusion 36.

With guidewire 60 in the position shown in FIG. 10, guidewire 60 may be used to direct other devices between occlusion 36 and adventitia 24. For example, a catheter may be advanced over guidewire 60 until the distal end of the catheter extends between an occlusion and the adventia. After reaching this location, the catheter may be used to dilate the tissue surrounding the catheter. Examples of catheters that may be used to dilate tissue include inflatable member catheters and atherectomy catheters.

Figure 11:
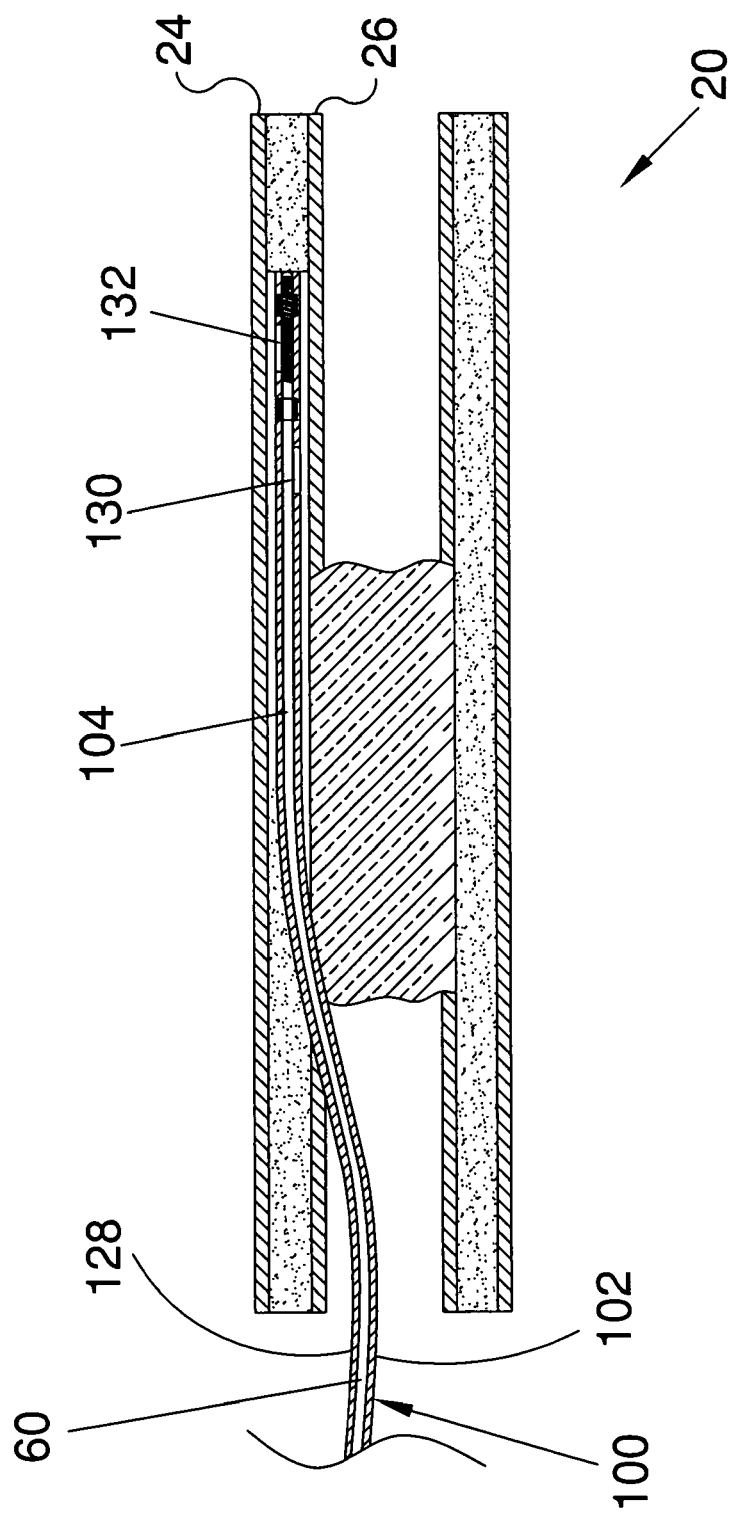
FIG. 11 is an additional view of the artery and the guidewire shown in the previous figure. In the embodiment of FIG. 11, an orienting device 100 been advanced over the guidewire.

FIG. 11 is an additional view of artery 20 and guidewire 60 shown in the previous figure. In the embodiment of FIG. 11, an orienting device 100 has been advanced over guidewire 60. Orienting device 100 includes a distal shaft 102 comprising a outer wall 128 defining a central lumen 104. A first aperture 130 and a second aperture 132 are also defined by outer wall 128. In the embodiment of FIG. 11, first aperture 130 and second aperture 132 are both in fluid communication with central lumen 104.

In the embodiment of FIG. 11, orienting device 100 has been positioned so that first aperture 130 opens toward intima 26 of artery 20 and second aperture 132 opens toward adventitia 24. In the embodiment of FIG. 11, first aperture 130 and second aperture 132 are longitudinally separated from one another. Orienting device 100 includes a first radiopaque marker that is located between first aperture 130 and second aperture 132. A second radiopaque marker of orienting device 100 is located distally of second aperture 132.

Figure 12:
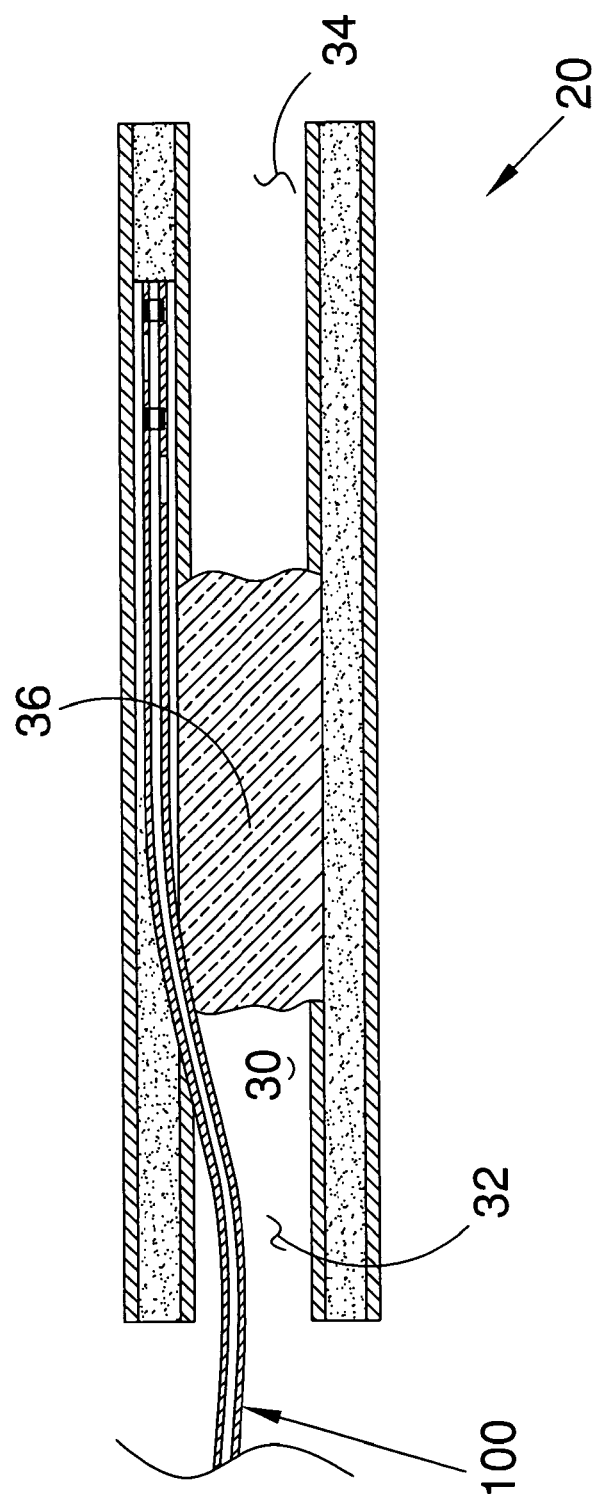
FIG. 12 is an additional view of the artery and the orienting device shown in the previous figure.

FIG. 12 is an additional view of artery 20 and orienting device 100 shown in the previous figure. In the embodiment of FIG. 12, guidewire 60 has been withdrawn leaving orienting device 100 in the position shown in FIG. 12. With reference to FIG. 12, it will be appreciated that orienting device 100 extends beyond occlusion 36. In FIG. 12, occlusion 36 is shown blocking true lumen 30. Occlusion 36 divides true lumen 30 into a proximal segment 32 and a distal segment 34. When an orienting device in accordance with some embodiments disclosed herein is advanced between the adventitia and the intima of an artery, the orienting device may be used to direct a re-entry device toward true lumen 30. Fluid communication between proximal segment 32 and distal segment 34 may be achieved by re-entering the true lumen with the re-entry device.

Figure 13:
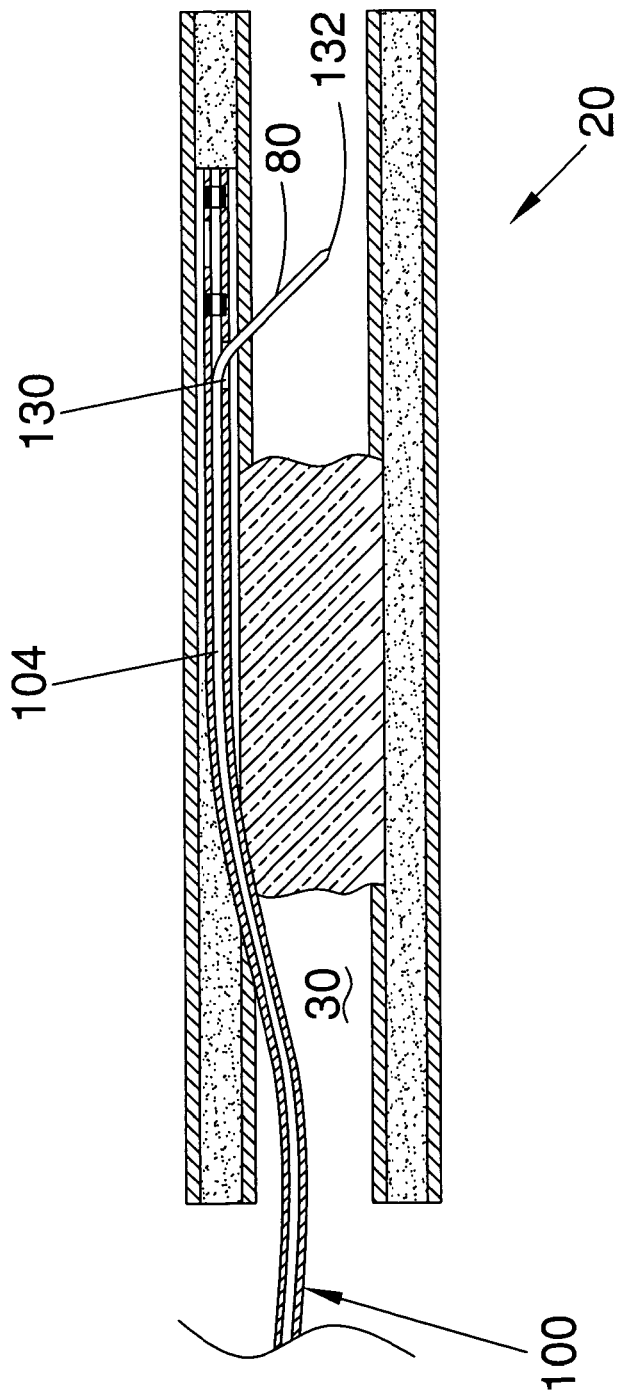
FIG. 13 is an additional view showing the orienting device shown in the previous figure. In the embodiment of FIG. 13 a re-entry device has been advanced into a central lumen of the orienting device. A distal end of the re-entry device has been advanced through a first aperture of the orienting device and can be seen residing in the true lumen.

FIG. 13 is an additional view of artery 20 and orienting device 100 shown in the previous figure. In the embodiment of FIG. 13, a re-entry device 80 has been advanced into central lumen 104 of orienting device 100. A distal end 132 of re-entry device 80 has been advanced through first aperture 130 and can be seen residing in true lumen 30.

After re-entry device 80 is positioned as shown in FIG. 13, orienting device 100 may be withdrawn leaving re-entry device 80 in the position shown in FIG. 13. Devices such as inflatable member angioplasty catheters and atherectomy catheters may then be advanced over re-entry device 80. In this way, these devices may be used in conjunction with re-entry device 80 to establish a blood flow path between proximal segment 32 of true lumen 30 and distal segment 34 of true lumen 30. This path allows blood to flow around occlusion 36.

Figure 14:
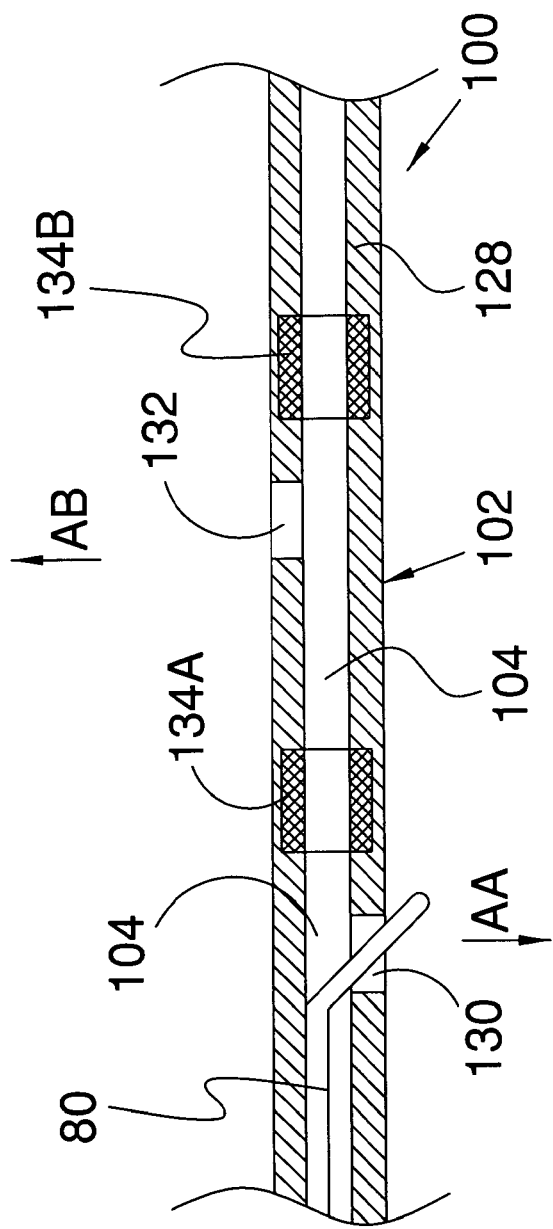
FIG. 14 is an enlarged cross-sectional view of the orienting device shown in the previous figure.

FIG. 14 is an enlarged cross-sectional view of orienting device 100 shown in the previous figure. Orienting device 100 includes a distal shaft 102 comprising an outer wall 128 defining a central lumen 104. Outer wall 128 defines a first aperture 130 and a second aperture 132 that are both in fluid communication with central lumen 104. In the embodiment of FIG. 14, first aperture 130 extends away from central lumen 104 in a first direction that is represented by a first arrow AA in FIG. 14. Second aperture 132 extends away from central lumen 104 in a second direction that is represented by a second arrow AB in FIG. 14. In FIG. 14, first arrow AA and second arrow AB extend in generally opposite directions. In FIG. 14, first arrow AA and second arrow AB are directed about 180 degrees away from one another.

In the embodiment of FIG. 14, first aperture 130 and second aperture 132 are longitudinally separated from one another. Orienting device 100 includes a first radiopaque marker 134A that is located between first aperture 130 and second aperture 132. A second radiopaque marker 134B of orienting device 100 is located distally of second aperture 132.

A re-entry device 80 is disposed in central lumen 104 of orienting device 100. In the embodiment of FIG. 14A, first radiopaque marker 134A, second radiopaque marker 134B and re-entry device 80 comprise radiopaque materials. Because of the radiopaque nature of their materials of construction, first radiopaque marker 134A, second radiopaque marker 134B, and re-entry device 80 will all be visible on a fluoroscopic display during a fluoroscopic procedure. The relative location of these radiopaque elements on the fluoroscopic display can be used to direct the distal end of re-entry device 80 through a selected aperture in orienting device 100.

Figure 15:
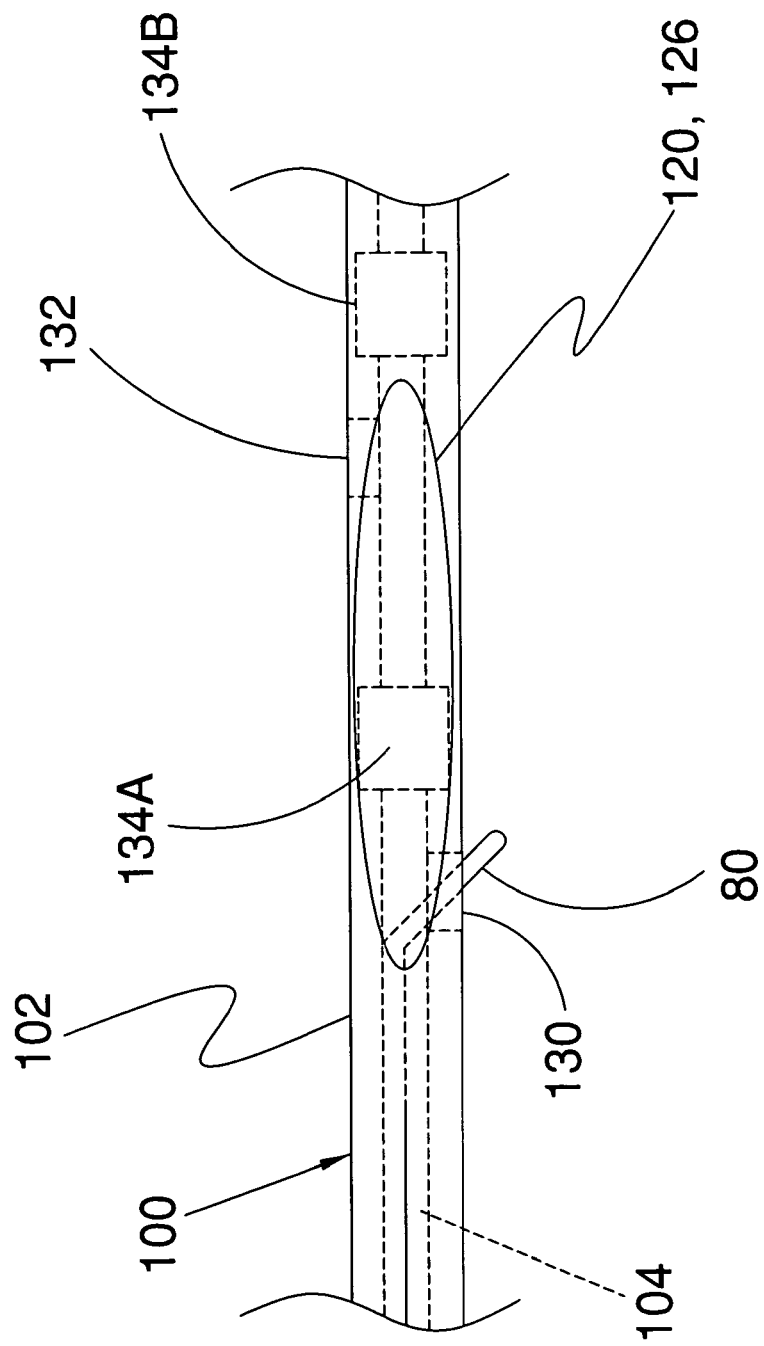
FIG. 15 is a stylized plan view showing the orienting device shown in the previous figure.

FIG. 15 is a stylized plan view showing orienting device 100 shown in the previous figure. In FIG. 15, a distal portion of re-entry device 80 can be seen extending through first aperture 130. First aperture 130 and second aperture 132 both fluidly communicate with central lumen 104 of orienting device 100. Orienting device 100 includes a first radiopaque marker 134A that is located between first aperture 130 and second aperture 132. A second radiopaque marker 134B of orienting device 100 is located distally of second aperture 132.

Orienting device 100 comprises an orienting element 120 that is fixed to a distal shaft 102. Orienting element 120 comprises an inflatable member 126. When inflatable member 126 of orienting element 120 is inflated between the adventicia and the intima of a blood vessel, orienting device 100 will orient itself within the blood vessel so that either first aperture 130 or second aperture 132 opens toward a true lumen of the artery. The physician may select the aperture opening toward the true lumen, for example, using the fluoroscopic methods described herein. The physician may then insert the distal end of re-entry device 80 through the selected aperture.

Figure 16:
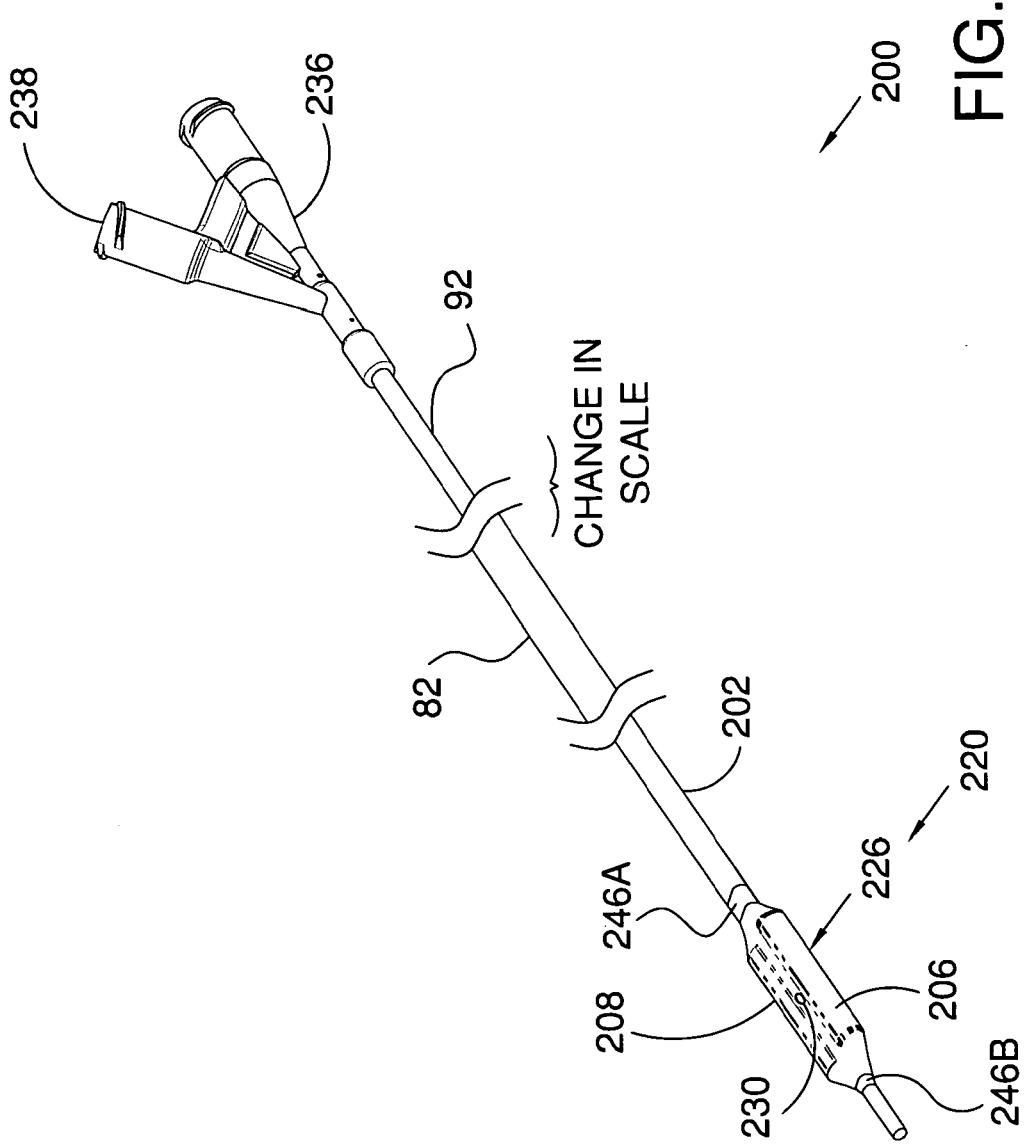
FIG. 16 is a perspective view of an additional exemplary embodiment of an orienting device.
Figure 21:
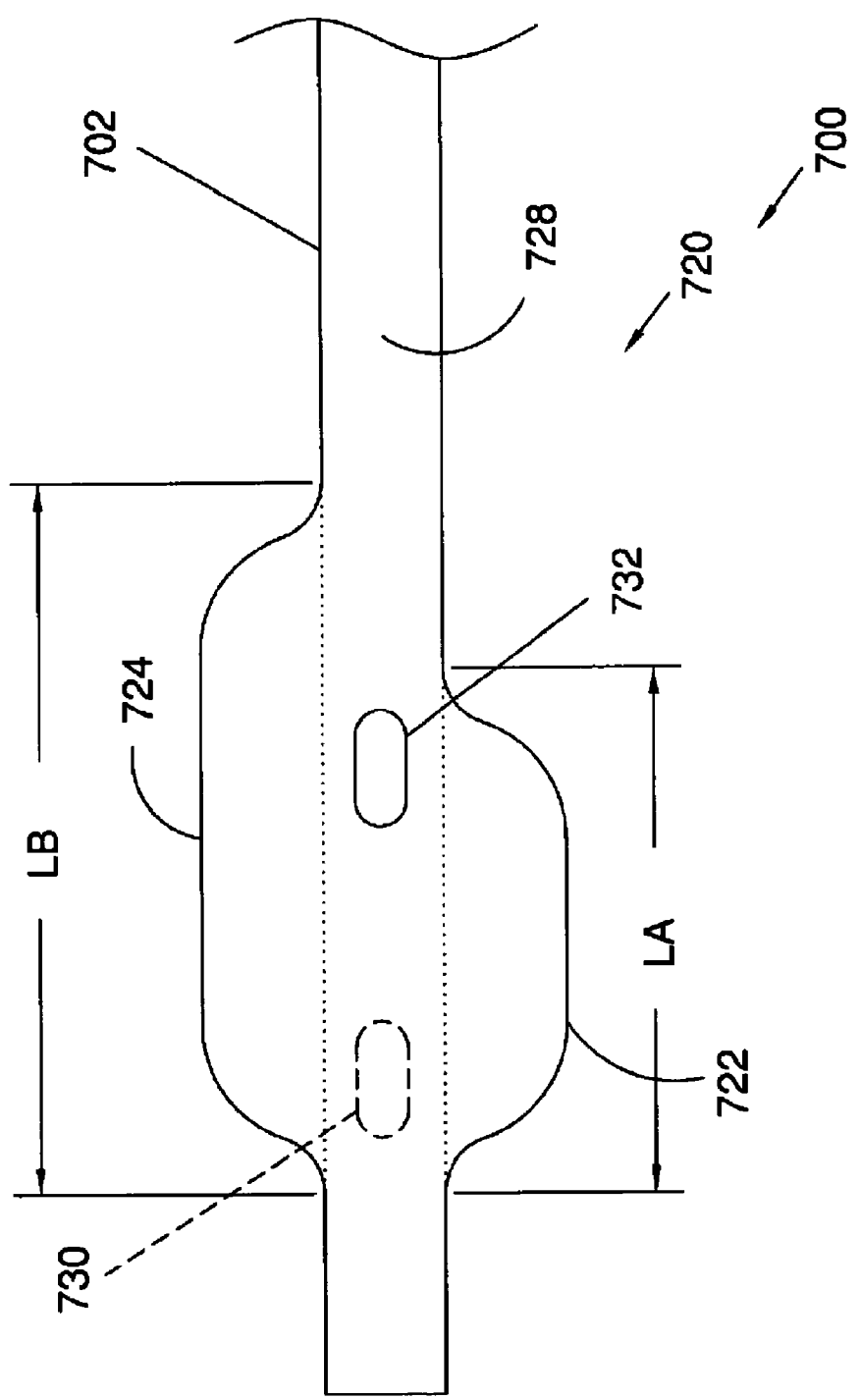
FIG. 21 is a plan view showing an additional exemplary orienting device.

FIG. 16 is a perspective view of an orienting device 200. Orienting device 200 comprises a distal shaft 202, a proximal shaft 92 and an intermediate shaft 82 that extends between distal shaft 202 and proximal shaft 92. Orienting device 200 includes an orienting element 220 that is coupled to a distal shaft 202. In the embodiment of FIG. 21, orienting element 220 comprises an inflatable member 226 that is fixed to distal shaft 202. Inflatable member 226 may be fixed to distal shaft 202, for example, at a proximal waist 246A, at a distal waist 246B, at the top of the inflatable member 226, and at the bottom of the inflatable member.

Orienting element 220 comprises a first portion 206 and a second portion 208. First portion 206 of orienting element 220 extends in a first direction away from distal shaft 202. Second portion 208 of orienting element 220 extends away from distal shaft 202 in a second direction that is generally opposite the first direction.

A hub 236 is fixed to the proximal end of proximal shaft 92. Hub 236 includes a proximal port 238. Proximal port 238 fluidly communicates with an interior of inflatable member 226 via inflation lumens defined by distal shaft 202, intermediate shaft 82, and proximal shaft 92. Inflatable member 226 may be inflated by injecting an inflation media into proximal port 238. Examples of inflation media that may be suitable in some applications include saline, carbon dioxide, or nitrogen. In some useful embodiments, inflatable member 226, distal shaft 202, intermediate shaft 82, and proximal shaft 92 comprise thermoplastic materials. Examples of thermoplastic materials that may be suitable in some applications include Nylon, Pebax, or P.E.T.

A first aperture 230 is disposed on a first side of orienting element 220. When inflatable member 226 of orienting element 220 is inflated between the adventicia and the intima of a blood vessel, orienting device 200 will orient itself within the blood vessel so that first aperture 230 either opens toward the true lumen of the artery or opens 180 degrees away from the true lumen of the artery. A second aperture is disposed on a second side of orienting element 220. Second aperture is not visible in FIG. 16. First aperture 230 is disposed on a first side of orienting element 220 and the second aperture is disposed on a second side of orienting element that is generally opposite the first side.

Figure 17:
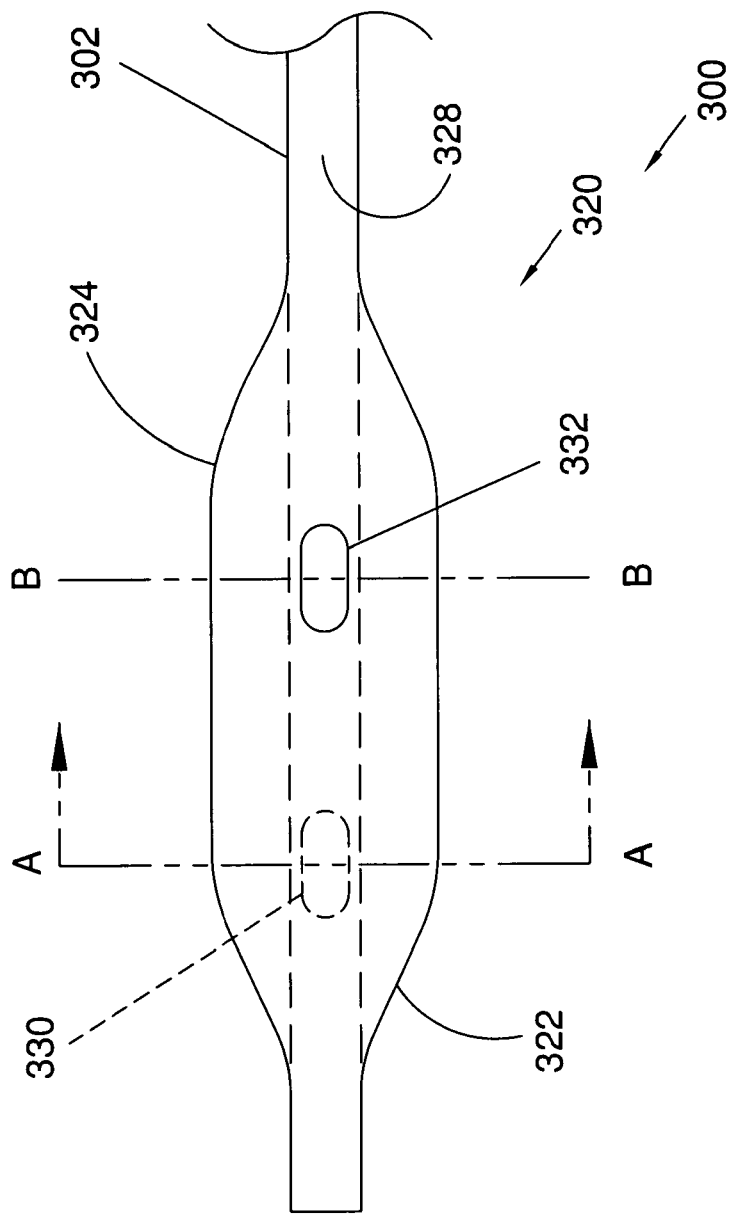
FIG. 17 is a plan view showing an additional exemplary orienting device.

FIG. 17 is a plan view showing an additional exemplary orienting device 300. Orienting device 300 of FIG. 17 comprises an orienting element 320 coupled to a distal shaft 302. In the embodiment of FIG. 17, orienting element 320 comprises a first inflatable member 322 and a second inflatable member 324. In the embodiment of FIG. 17, first inflatable member 322 and second inflatable member 324 are both formed from extruded portions of an outer wall 328 of distal shaft 302. Outer wall 328 defines a first aperture 330 and a second aperture 332. With reference to FIG. 17, it will be appreciated that first aperture 330 and second aperture 332 are both disposed between first inflatable member 322 and second inflatable member 324.

Figure 18:
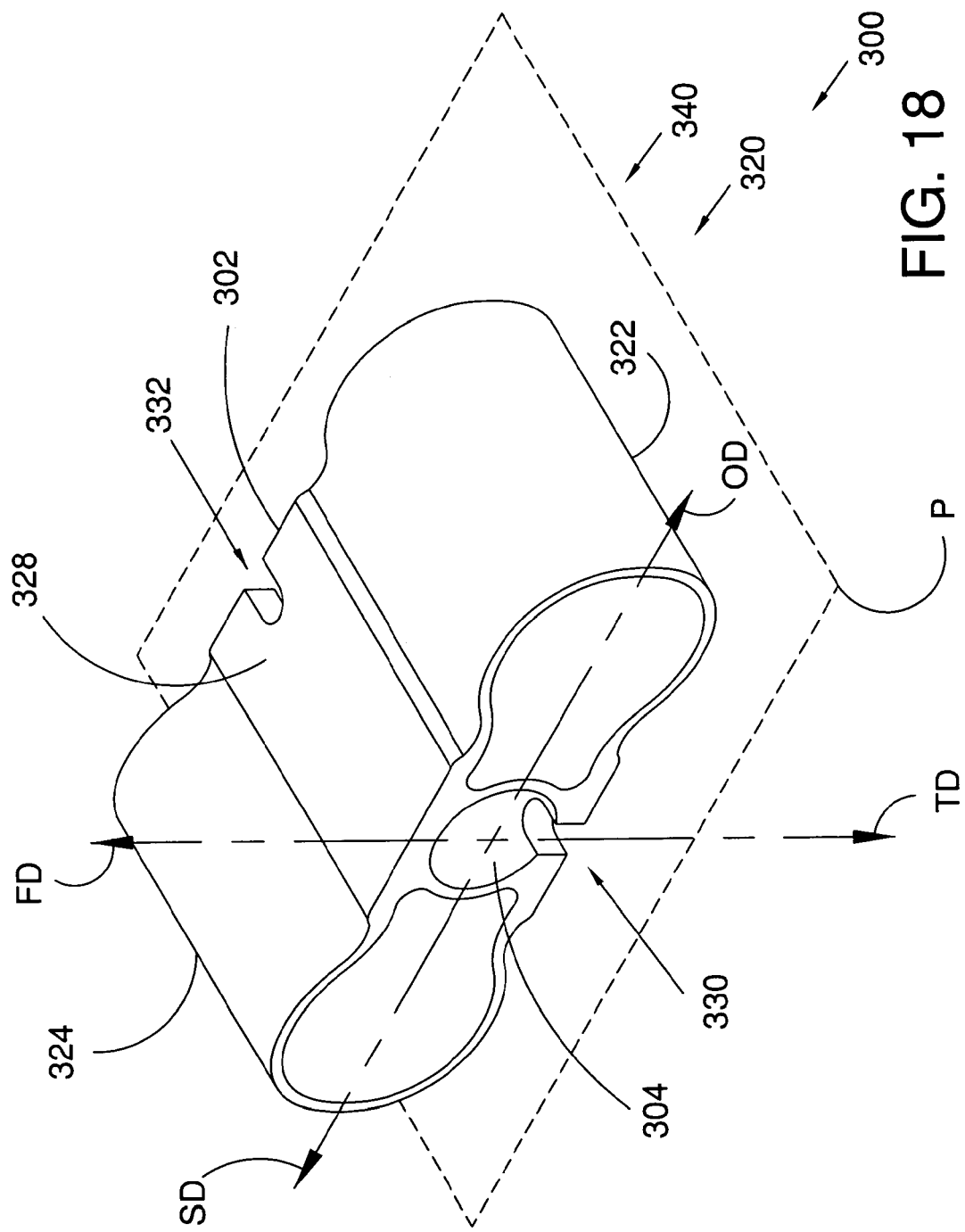
FIG. 18 is a stylized perspective view showing a portion of the orienting device shown in the previous figure. For purposes of illustration, the portion shown in FIG. 18 is created by cutting the orienting device along cutting plane A-A and cutting plane B-B shown in the previous figure.

FIG. 18 is a stylized perspective view showing a portion 340 of orienting device 300 shown in the previous figure. Portion 340 is created by cutting orienting device 300 along cutting plane A-A and cutting plane B-B shown in the previous figure.

Orienting device 300 comprises an orienting element 320 that is coupled to a distal shaft 302. Orienting element 320 comprises a first inflatable member 322 and a second inflatable member 324. First inflatable member 322 of orienting element 320 extends in a first direction away from distal shaft 302. Second inflatable member 324 of orienting element 320 extends away from distal shaft 302 in a second direction that is generally opposite the first direction.

With reference to FIG. 18, it will be appreciated that first inflatable member 322 extends away from outer wall 328 in a first direction that is represented by an arrow labeled OD. With continuing reference to FIG. 18, it will be appreciated that second inflatable member 324 extends way from distal shaft 302 in a second direction that is generally opposite the first direction. In FIG. 18, the second direction is represented by an arrow labeled SD.

With reference to FIG. 18, it will be appreciated that an outer wall 328 of distal shaft 302 defines a first aperture 330 and a second aperture 332. First aperture 330 extends away from central lumen 304 in a third direction that is represented by an arrow labeled TD. With continuing reference to FIG. 18, it will be appreciated that second aperture 332 extends away from central lumen 304 in a forth direction that is generally opposite the third direction. In FIG. 18, the fourth direction is represented by an arrow labeled FD.

With reference to FIG. 18, it will be appreciated that first aperture 330 and second aperture 332 are both disposed between first inflatable member 322 and second inflatable member 324. First aperture 330 and second aperture 332 both fluidly communicate with a central lumen 304 defined by distal shaft 302. First aperture 330 and second aperture 332 are generally oriented at a right angle to a plane P defined by first inflatable member 322 and second inflatable member 324 of orienting element 320.

Figure 19:
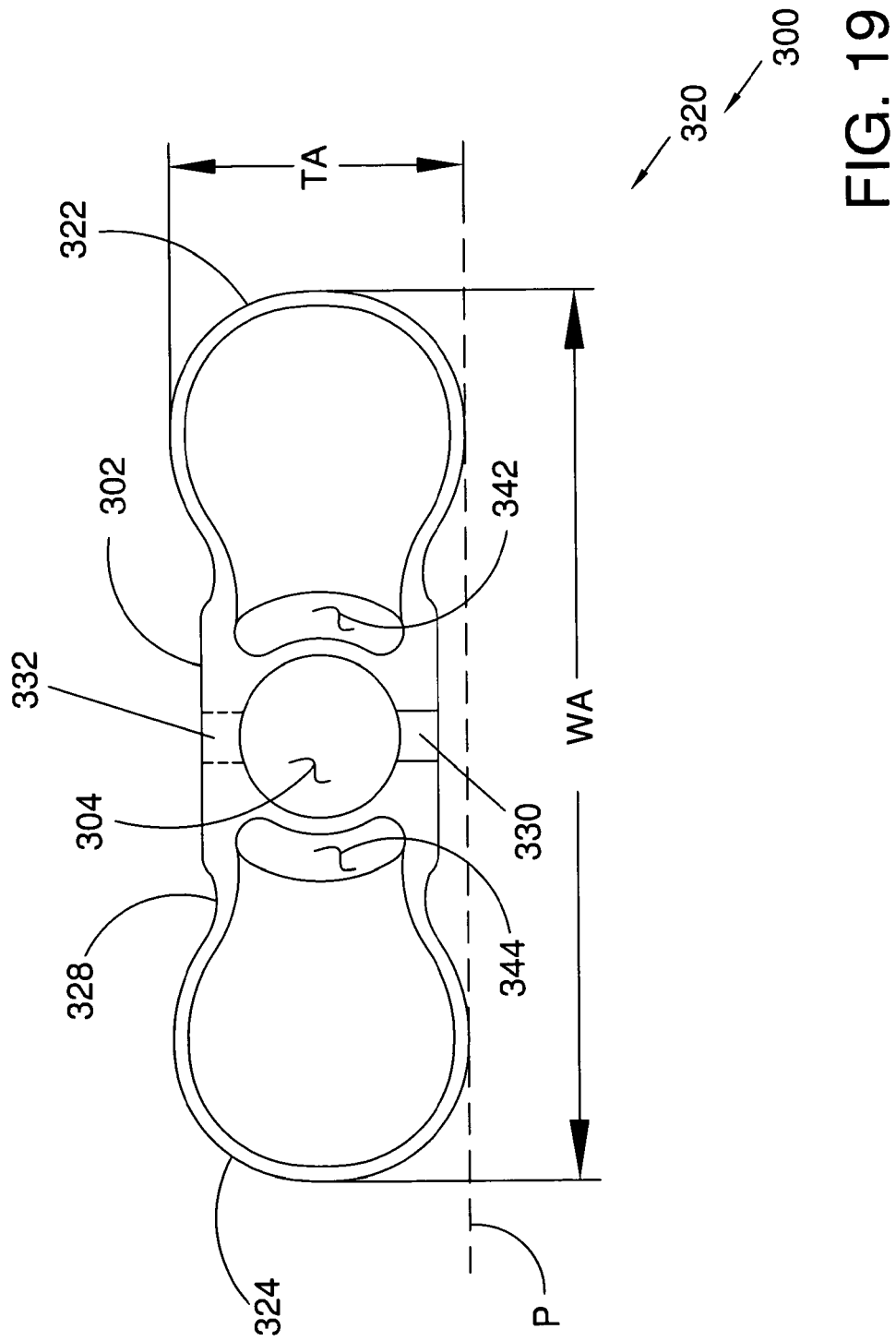
FIG. 19 is a stylized cross-sectional view showing the orienting device shown in the previous figure. In the embodiment of FIG. 20, an orienting element of the orienting device is assuming a deployed shape.

FIG. 19 is a stylized cross-sectional view showing orienting device 300 shown in the previous figure. With reference to FIG. 19, it will be appreciated that distal shaft 302 defines a central lumen 304, a first planetary lumen 342, a second planetary lumen 344. The planetary lumens are defined in part by an outer wall 328 of distal shaft 302. Outer wall 328 also defines a first aperture 330 and a second aperture 332. First aperture 330 and second aperture 332 both fluidly communicate with central lumen 304.

Orienting device 300 comprises an orienting element 320 that includes a first inflatable member 322 and a second inflatable member 324. In the embodiment of FIG. 19, first inflatable member 322 is formed of an extruded portion of outer wall 328 of distal shaft 302. First inflatable member 322 defines an interior that is in fluid communication with first planetary lumen 342. In the embodiment of FIG. 19, first inflatable member 322 and distal shaft 302 are monolithic. As shown in FIG. 19, first inflatable member 322 and outer wall 328 of distal shaft 302 are seamlessly formed from a single piece of material. With reference to FIG. 19, it will be appreciated that second inflatable member 324 defines an interior that is in fluid communication with second planetary lumen 344. In the embodiment of FIG. 19, second inflatable member 324 comprises an extruded portion of outer wall 328 of distal shaft 302.

One potential advantage of creating an orienting element from a monolithic tube is the elimination of fixation points between the orienting element and catheter shaft thus reducing processing steps and manufacturing cost. Another potential advantage is the reduction of fixation points between the orienting element and catheter shaft which may also reduce the distal diameter of the catheter by eliminating areas of overlapping material. Another potential advantage may include the reduction of potential failure points through the elimination of fixation points (e.g. thermal or adhesive bonds) between the orienting element and the catheter shaft.

First inflatable member 322 of orienting element 320 extends in a first direction away from distal shaft 302. Second inflatable member 324 of orienting element 320 extends away from distal shaft 302 in a second direction that is generally opposite the first direction.

In the embodiment of FIG. 19, orienting element 320 is assuming a deployed shape. Also in the embodiment of FIG. 19, first inflatable member 322 and second inflatable member 324 are both in a generally inflated state. With reference to FIG. 19, it will be appreciated that first inflatable member 322 and second inflatable member 324 define a plane P. With continuing reference to FIG. 19, it will be appreciated that orienting element 320 has a first width WA and first thickness TA. In the embodiment of FIG. 19, first width WA is greater than first thickness TA when orienting element 320 is assuming a deployed shape.

In some useful embodiments, an aspect ratio of first width WA to first thickness TA is greater than about one when orienting element 320 is assuming a deployed shape. In some particularly useful embodiments, the aspect ratio of first width WA to first thickness TA is greater than about two when orienting element 320 is assuming a deployed shape. In some especially useful embodiments, the aspect ratio of first width WA to first thickness TA is greater than about three when orienting element 320 is assuming a deployed shape.

Figure 20:
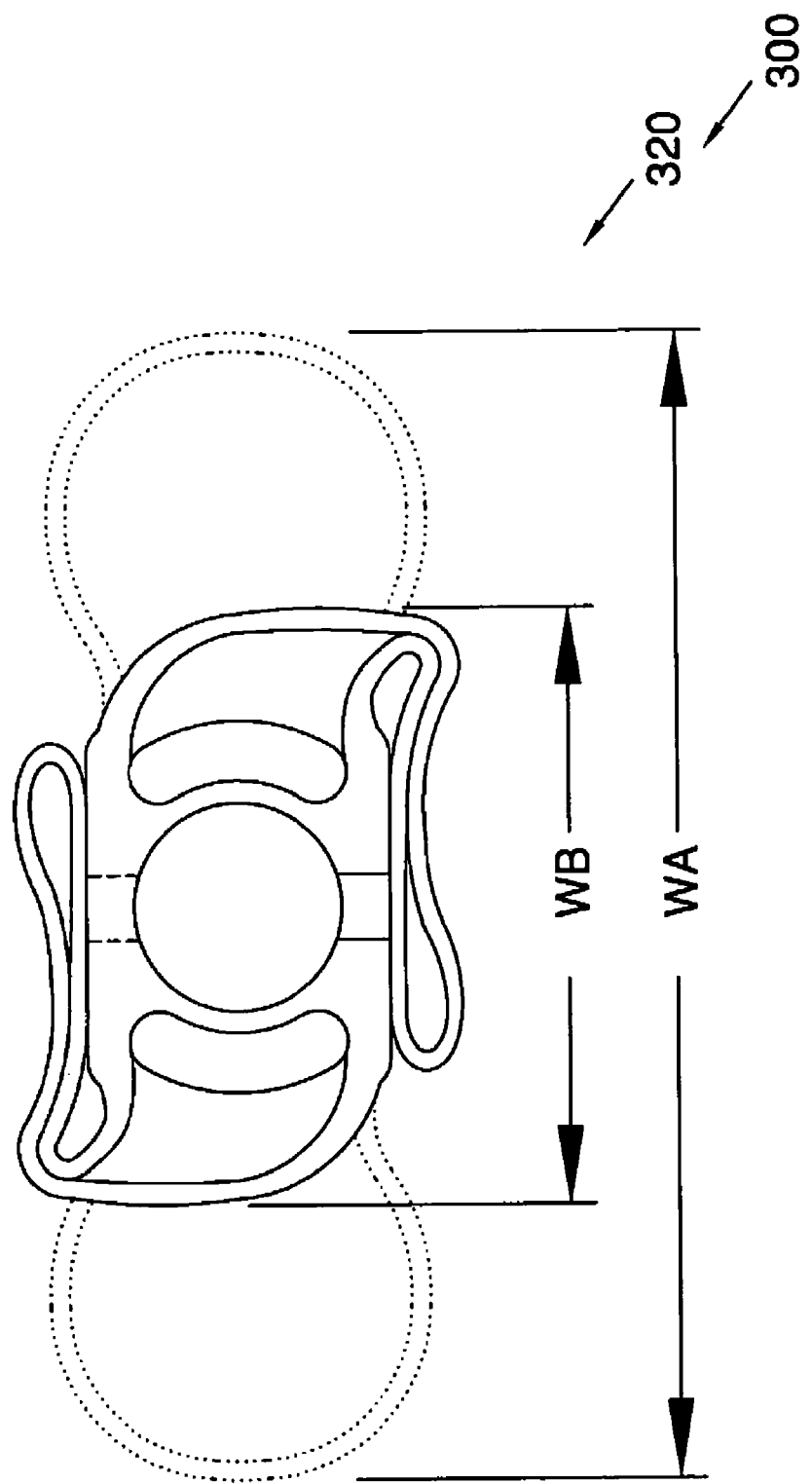
FIG. 20 is an additional stylized cross-sectional view showing the orienting device shown in the previous figure. In the embodiment of FIG. 20, an orienting element of the orienting device is assuming a generally collapsed shape.

FIG. 20 is an additional stylized cross-sectional view showing orienting device 300 shown in the previous figure. In the embodiment of FIG. 20, orienting element 320 is assuming a generally collapsed shape and the inflatable members are in a substantially deflated state. When the inflatable members are deflated, orienting element 320 may assume various collapsed and/or folded shapes. In the embodiment of FIG. 20, orienting element 320 has a second width WB.

A deployed shape of orienting element 320 is shown with dotted lines in FIG. 20. With reference to FIG. 20, it will be appreciated that orienting element 320 has a first width WA that is greater than second width WB when orienting element 320 is assuming a deployed shape.

FIG. 21 is a plan view showing an additional exemplary orienting device 700. Orienting device 700 of FIG. 21 comprises an orienting element 720 coupled to a distal shaft 702. In the embodiment of FIG. 21, orienting element 720 comprises a first inflatable member 722 and a second inflatable member 724. In the embodiment of FIG. 21, first inflatable member 722 and second inflatable member 724 are both formed from extruded portions of an outer wall 728 of distal shaft 702. Outer wall 728 defines a first aperture 730 and a second aperture 732. With reference to FIG. 21, it will be appreciated that first aperture 730 and second aperture 732 are both disposed between first inflatable member 722 and second inflatable member 724.

With reference to FIG. 21, it will be appreciated that first inflatable member 722 has a first length LA and second inflatable member 724 has a second length LB. In the embodiment of FIG. 21, second length LB is greater than first length LA. In one useful method, first inflatable member 722 and second inflatable member 724 are both inflated with a radiopaque inflation media. When this is the case, a physician may use fluoroscopic visualization techniques to determine the orientation of orienting device 700 by observing first inflatable member 722 and second inflatable member 724 on the fluoroscopic display.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

The invention claimed is:

1. A method, comprising:
    positioning an orienting element mounted on a catheter shaft between an occlusion and an adventitia of a blood vessel;
    inflating an inflatable member of the orienting element to orient the catheter shaft relative to a true lumen of the blood vessel, wherein inflating the inflatable member causes the catheter shaft to rotate about a central longitudinal axis of the catheter shaft; and
    advancing a re-entry device through a lumen of the catheter shaft such that a distal end of the re-entry device extends out a first aperture of the catheter shaft toward the true lumen of the blood vessel;
    wherein the first aperture is substantially orthogonal to a plane defined by the orienting element.

2. The method of claim 1, wherein the central longitudinal axis extends parallel to the plane defined by the orienting element.

3. The method of claim 1, wherein the first aperture extends through a sidewall of the catheter shaft.

4. The method of claim 3, wherein the first aperture is positioned between a first balloon of the inflatable member and a second balloon of the inflatable member.

5. The method of claim 4, wherein the first and second balloons inflate in generally opposite directions along the plane.

6. The method of claim 3, further comprising a second aperture extending through the sidewall of the catheter shaft.

7. The method of claim 6, wherein the first and second apertures are positioned on opposing sides of the catheter shaft.

8. The method of claim 6, wherein the first aperture is axially offset from the second aperture.

9. The method of claim 1, further comprising advancing the catheter shaft over a guidewire to position the orienting element between the occlusion and the adventitia of the blood vessel.

10. The method of claim 9, wherein the guidewire is positioned in the lumen of the catheter shaft.

11. The method of claim 10, further comprising:
    withdrawing the guidewire from the lumen of the catheter shaft prior to advancing the re-entry device through the lumen of the catheter shaft.

12. A method, comprising:
    advancing a catheter including a catheter shaft and an inflatable member mounted on a distal region thereof over a guidewire to position the inflatable member between an occlusion and an adventitia of a blood vessel, the catheter including a first lateral aperture;
    inflating the inflatable member to orient the first lateral aperture toward a true lumen of the blood vessel; and
    advancing a re-entry device through a lumen of the catheter shaft such that a distal end of the re-entry device extends out the first aperture of the catheter toward the true lumen of the blood vessel;
    wherein inflating the inflatable member causes the catheter to rotate about a central longitudinal axis of the catheter.

13. The method of claim 12, wherein the first aperture extends through a sidewall of the catheter shaft.

14. The method of claim 13, wherein the first aperture is positioned between a first balloon of the inflatable member and a second balloon of the inflatable member.

15. The method of claim 14, wherein the first and second balloons inflate in generally opposite directions along a plane passing through the central longitudinal axis.

16. The method of claim 14, further comprising a second aperture extending through the sidewall of the catheter shaft.

17. The method of claim 16, wherein the first and second apertures are positioned on opposing sides of the catheter shaft.

18. The method of claim 17, wherein the first aperture is axially offset from the second aperture.

19. The method of claim 16, wherein the first and second apertures both open into the lumen of the catheter shaft.

* * * * *